(12) United States Patent
Muir et al.

(10) Patent No.: US 8,685,702 B2
(45) Date of Patent: Apr. 1, 2014

(54) COMPOSITIONS AND METHODS FOR IMPROVED ISOPRENE PRODUCTION USING TWO TYPES OF ISPG ENZYMES

(75) Inventors: Rachel E. Muir, Redwood City, CA (US); Walter Weyler, San Francisco, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 13/335,768

(22) Filed: Dec. 22, 2011

(65) Prior Publication Data

US 2012/0164711 A1 Jun. 28, 2012

Related U.S. Application Data

(60) Provisional application No. 61/426,505, filed on Dec. 22, 2010.

(51) Int. Cl.
| | | |
|---|---|---|
| C12N 1/20 | (2006.01) | |
| C12N 1/00 | (2006.01) | |
| C12P 5/02 | (2006.01) | |
| C12N 9/02 | (2006.01) | |
| C07H 21/04 | (2006.01) | |

(52) U.S. Cl.
USPC .............. 435/252.3; 435/252.33; 435/252.34; 435/252.35; 435/254.2; 435/254.7; 435/167; 435/183; 435/243; 536/23.2

(58) Field of Classification Search
None
See application file for complete search history.

(56) References Cited

U.S. PATENT DOCUMENTS

| | | | |
|---|---|---|---|
| 4,570,029 A | 2/1986 | Kulprathipanja et al. | |
| 4,683,202 A | 7/1987 | Mullis | |
| 4,703,007 A | 10/1987 | Mulholland et al. | |
| 5,849,970 A | 12/1998 | Fall et al. | |
| 5,874,276 A | 2/1999 | Fowler et al. | |
| 6,022,725 A | 2/2000 | Fowler et al. | |
| 6,106,888 A | 8/2000 | Dale et al. | |
| 6,176,176 B1 | 1/2001 | Dale et al. | |
| 6,268,328 B1 | 7/2001 | Mitchinson et al. | |
| 6,316,695 B1 | 11/2001 | Han et al. | |
| 6,998,471 B2 | 2/2006 | Hallahan et al. | |
| 7,129,392 B2 | 10/2006 | Hahn et al. | |
| 7,132,527 B2 | 11/2006 | Payne et al. | |
| 7,241,587 B2 | 7/2007 | Dodge et al. | |
| 7,262,041 B2 | 8/2007 | Baldwin et al. | |
| 7,659,097 B2 | 2/2010 | Renninger et al. | |
| 8,173,410 B2 | 5/2012 | Bott et al. | |
| 2005/0079617 A1 | 4/2005 | Cervin et al. | |
| 2005/0287625 A1 | 12/2005 | Miller, Jr. et al. | |
| 2008/0038805 A1 | 2/2008 | Melis | |
| 2008/0274523 A1 | 11/2008 | Renninger et al. | |
| 2009/0137014 A1 | 5/2009 | Tsuruta et al. | |
| 2009/0203102 A1 | 8/2009 | Cervin et al. | |
| 2009/0282545 A1 | 11/2009 | Eichelberger et al. | |
| 2010/0048964 A1 | 2/2010 | Calabria et al. | |
| 2010/0086978 A1 | 4/2010 | Beck et al. | |
| 2010/0113846 A1 | 5/2010 | McAuliffe et al. | |
| 2010/0167370 A1 | 7/2010 | Chotani et al. | |
| 2010/0167371 A1 | 7/2010 | Chotani et al. | |
| 2010/0178679 A1* | 7/2010 | Anthony et al. .............. 435/167 |
| 2010/0184178 A1 | 7/2010 | Beck et al. | |
| 2010/0297749 A1 | 11/2010 | Aravanis et al. | |
| 2011/0014672 A1 | 1/2011 | Chotani et al. | |
| 2011/0045563 A1 | 2/2011 | Melis | |
| 2011/0178261 A1 | 7/2011 | Feher et al. | |
| 2012/0329102 A1 | 12/2012 | McAuliffe et al. | |

FOREIGN PATENT DOCUMENTS

| | | |
|---|---|---|
| EP | 0 215 594 A2 | 3/1987 |
| EP | 0 215 594 A3 | 3/1987 |
| EP | 0 215 594 B1 | 3/1987 |
| EP | 0 215 594 B2 | 3/1987 |
| EP | 0 238 023 A2 | 9/1987 |
| EP | 0 238 023 A3 | 9/1987 |
| EP | 0 238 023 B1 | 9/1987 |
| EP | 0 238 023 B2 | 9/1987 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| WO | WO-95/04134 A1 | 2/1995 |
| WO | WO-96/35796 A1 | 11/1996 |
| WO | WO-98/02550 A2 | 1/1998 |
| WO | WO-98/02550 A3 | 1/1998 |
| WO | WO-2004/033646 A2 | 4/2004 |
| WO | WO-2004/033646 A3 | 4/2004 |
| WO | WO-2005/001036 A2 | 1/2005 |
| WO | WO-2005/001036 C1 | 1/2005 |
| WO | WO-2008/003078 A2 | 1/2008 |
| WO | WO-2008/003078 A3 | 1/2008 |
| WO | WO-2008/003078 A8 | 1/2008 |

(Continued)

OTHER PUBLICATIONS

Akhtar, M.K. et al. (2008). "Deletion of iscR Stimulates Recombinant Clostridial Fe—Fe Hydrogenase Activity and $H_2$-accumulation in Escherichia coli BL21 (DE3)," Applied Microbiol. Biotechnol. 78(5):853-862.

Anderson, M.S. et al. (Nov. 15, 1989). "Isopentenyl Diphosphate: Dimethylallyl Diphosphate Isomerase. An Improved Purification of the Enzyme and Isolation of the Gene from Saccharomyces cerevisiae," J. Biol. Chem. 264(32):19169-19175.

Baba, T. et al. (2006). "Construction of Escherichia coli K-12 In-Frame, Single-Gene Knockout Mutants: the Keio Collection," Mol. Syst. Biol., 2006.0008:1-11.

Bellion, E. et al. (1993). "Methylamine Utilization in Yeast and Bacteria: Studies Using in vivo NMR," Chapter 32 in Microbial Growth on $C_1$ Compounds, Muerrell, J.C. et al. eds, Intercept Ltd: Andover, UK, pp. 415-432.

(Continued)

Primary Examiner — Iqbal H Chowdhury
(74) Attorney, Agent, or Firm — Morrison & Foerster LLP

(57) ABSTRACT

The invention provides for compositions and methods for producing isoprene by using recombinantly engineered cells that utilize a system of dual IspG enzymes in addition to isoprene synthase.

20 Claims, 4 Drawing Sheets

(56) References Cited

FOREIGN PATENT DOCUMENTS

| | | |
|---|---|---|
| WO | WO-2008/128159 A1 | 10/2008 |
| WO | WO-2009/041581 A1 | 4/2009 |
| WO | WO-2009/076676 A2 | 6/2009 |
| WO | WO-2009/076676 A3 | 6/2009 |
| WO | WO-2009/079448 A2 | 6/2009 |
| WO | WO-2009/079448 A3 | 6/2009 |
| WO | WO-2009/132220 A2 | 10/2009 |
| WO | WO-2009/132220 A3 | 10/2009 |
| WO | WO-2010/003007 A2 | 1/2010 |
| WO | WO-2010/003007 A3 | 1/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031076 A3 | 3/2010 |
| WO | WO-2010/031077 A1 | 3/2010 |
| WO | WO-2010/031079 A1 | 3/2010 |
| WO | WO-2010/078457 A2 | 7/2010 |
| WO | WO-2010/078457 A3 | 7/2010 |
| WO | WO-2010/124146 A2 | 10/2010 |
| WO | WO-2010/124146 A3 | 10/2010 |
| WO | WO-2010/148150 A1 | 12/2010 |
| WO | WO-2010/148256 A1 | 12/2010 |
| WO | WO-2011/034863 A1 | 3/2011 |
| WO | WO-2012/058494 A2 | 5/2012 |
| WO | WO-2012/058494 A3 | 5/2012 |
| WO | WO-2012/088450 A1 | 6/2012 |
| WO | WO-2012/088462 A1 | 6/2012 |

OTHER PUBLICATIONS

Bennett, J.W. et al. eds. (1991). "Gene Cloning and Analysis," Chapter 3 in *More Gene Manipulations in Fungi*, Academic Press, San Diego, CA pp. 70-76.

Berka, R.M. et al. (1989). "The Development of Gene Expression Systems for Filamentous Fungi," *Biotechnology Advances* 7(2):127-154.

Bhayana, V. et al. (Jun. 1984). "Amino Acid Sequence of *Escherichia coli* Citrate Synthase," *Biochemistry* 23(13):2900-2905.

Bitoun, J.P. et al. (Dec. 2008). "*Escherichia coli* FtnA Acts as an Iron Buffer for Re-assembly of Iron-Sulfur Clusters in Response to Hydrogen Peroxide Stress," *Biometals* 21(6):693-703.

Boel, E. et al. (1984). "Two Different Types of Intervening Sequences in the Glucoamylase Gene from *Aspergillus niger*," *The EMBO Journal* 3(7):1581-1585.

Bologna, F.P. et al. (Aug. 2007). "*Escherichia coli* Malic Enzymes: Two Isoforms with Substantial Differences in Kinetic Properties, Metabolic Regulation, and Structure," *Journal of Bacteriology* 189(16):5937-5946.

Bouvier, F. et al. (2005). "Biogenesis, Molecular Regulation and Function of Plant Isoprenoids," *Progress in Lipid Res.* 44:357-429.

Broun, P. et al. (Nov. 13, 1998). "Catalytic Plasticity of Fatty Acid Modification Enzymes Underlying Chemical Diversity of Plant Lipids," *Science* 282:1315-1317.

Brown, L. et al. (Aug. 26, 1996). "Enzymatic Saccharification of Lignocellulosic Biomass," *NREL, Ethanol Project, Chemical Analysis and Testing Task, LAP-009*, pp. 1-8.

Bukau, B. et al. (Feb. 6, 1998). "The Hsp70 and Hsp60 Chaperone Machines," *Cell* 92:351-366.

Bunch, P.K. et al. (1997). "The *IdhA* Gene Encoding the Fermentative Lactate Dehydrogenase of *Escherichia coli*," *Microbiology* 143:187-195.

Campbell, E.I. et al. (1989). "Improved Transformation Efficiency of *Aspergillus niger* Using the Homologus *niaD* Gene for Nitrate Reductase," *Curr. Genet.* 16:53-56.

Cao, Q-N. et al. (2000). "Penicillopepsin-JT2, a Recombinant Enzyme from *Penicillium janthinellum* and the Contribution of a Hydrogen Bond in Subsite $S_3$ to $k_{cat}$," *Protein Science* 9:991-1001.

Chao, Y-P. et al. (2002). "Stringent Regulation and High-Level Expression of Heterologous Genes in *Escherichia coli* Using T7 System Controllable by the *araBAD* Promoter," *Biotechnol. Prog.* 18(2):394-400.

Chen, J-S. et al. (Feb. 1979). "A Simple Hydrogenase-Linked Assay for Ferredoxin and Flavodoxin," *Analytical Biochemistry* 93(1):216-222.

Chica, R.A. et al. (2005, e-pub Jul. 1, 2005 ). "Semi-Rational Approaches to Engineering Enzyme Activity: Combining the Benefits of Directed Evolution and Rational Design," *Current Opinion in Biotechnology* 16:378-384.

Cirino, P.C. et al. (Dec. 20, 2006, e-pub Jul. 12, 2006). "Engineering *Escherichia coli* for Xylitol Production From Glucose-Xylose Mixtures," *Biotechnology and Bioengineering* 95(6):1167-1176.

Devos, D. et al. (2000). "Practical Limits of Function Prediction," *Proteins: Structure, Function, and Genetics* 41:98-107.

Dhe-Paganon, S. et al. (1994). "Mechanism of Mevalonate Pyrophosphate Decarboxylase: Evidence for a Carbocationic Transition State," *Biochemistry* 33(45):13355-13362.

Djaman, O. et al. (Oct. 22, 2004). "Repair of Oxidized Iron-Sulfur Clusters in *Escherichia coli*," *J. of Biol. Chem.* 279(43):44590-44599.

Duckworth, H.W. et al. (1987). "Structural Basis for Regulation in Gram-Negative Bacterial Citrate Synthases," *Biochem. Soc. Symp.* 54:83-92.

EcoCyc. (2005) "ribF-ileS-IspA-fkpB-ispH 5-gene operon," located at <http://ecocyc.org/ECOLI/substring-search?type=NIL&object-+ribF-ileS-IspA-fkpB-ispH+,> last visited on May 29, 2012, three pages.

Eppler, T. et al. (1999). "Glycerol-3-Phosphate-Mediated Repression of *malT* in *Escherichia coli* Does Not Require Metabolism, Depends on Enzyme $IIA^{Glc}$ and is Mediated by cAMP Levels," *Molecular Microbiology* 33(6):1221-1231.

Finkelstein, D.B. (1992). "Transformation," Chapter 6 in *Biotechnology of Filamentous Fungi*, Butterworth-Heinemann: Boston, MA, pp. 113-156.

Fraenkel, D.G. (Apr. 1968). "Selection of *Escherichia coli* Mutants Lacking Glucose-6-Phosphate Dehydrogenase or Gluconate-6-Phosphate Dehydrogenase," *J. Bacteriol.* 95(4):1267-1271.

GenBank Accession No. AAQ84170, last updated on Feb. 15, 2005, located at <http://www.ncbi.nlm.nih.gov/protein/AAQ84170>, last visited on Dec. 22, 2011, 2 pages.

GenBank Accession No. AJ457070, last updated on Apr. 15, 2005, located at <http://www.ncbi.nlm.nih.gov/nuccore/38092202>, last visited on Jun. 2, 2010, 2 pages.

GenBank Accession No. AY182241, last updated on May 4, 2004, located at <http://www.ncbi.nlm.nih.gov/nuccore/32265057>, last visited on Jun. 2, 2010, 2 pages.

GenBank Accession No. AY279379, last updated on Mar. 11, 2005, located at <http://www.ncbi.nlm.nih.gov/nuccore/30984014>, last visited on Jun. 2, 2010, 2 pages.

GenBank Accession No. AY316691, last updated on Feb. 15, 2005, located at <http://www.ncbi.nlm.nih.gov/nuccore/35187003>, last visited on Jun. 2, 2010, 2 pages.

GenBank Accession No. AY341431, last updated on Feb. 15, 2005, located at <http://www.ncbi.nlm.nih.gov/nuccore/AY341431>, last visited on Feb. 27, 2012, 2 pages.

GenBank Accession No. CAC35696, last updated Apr. 15, 2005, located at <http://www.ncbi.nlm.nih.gov/protein/CAC35696>, last visited on Nov. 1, 2011, 1 page.

GenBank Accession No. CP001164, last updated Dec. 14, 2011, located at <http://www.ncbi.nim.nih.gov/protein/CP001164> last visted on May 29, 2012, seventy-six pages.

GenBank Accession No. D86235, last updated Oct. 29, 1997, located at <http://www.ncbi.nlm.nih.gov/nuccore/D86235> last visited on Feb. 27, 2012, two pages.

GenBank Accession No. E02927, last updated Nov. 4, 2005, located at <http://www.ncbi.nlm.nih.gov/nuccore/E02927> last visited on May 29, 2012, one page.

GenBank Accession No. NC_001416, last updated Mar. 11, 2011, located at <http://www.ncbi.nlm.nih.gov/nuccore/NC_001416> last visited on Feb. 8, 2013, forty-two pages.

GenomeNet (2012). "Steroid Biosynthesis—Reference Pathway," in KEGG: Kyoto Encyclopedia of Genes and Genomes, located at <http://www.genome.jp/kegg/pathway/map/map00100.html>, last visited on Dec. 28, 2012, 1 page.

(56) References Cited

OTHER PUBLICATIONS

Goedegebuur, F. et al. (2002, e-pub May 7, 2002). "Cloning and Relational Analysis of 15 Novel Fungal Endoglucanases from Family 12 Glycosyl Hydrolase," *Curr. Genet.* 41:89-98.

Gräwert, T. et al. (Oct. 13, 2004, e-pub. Sep. 21, 2004). "IspH Protein of *Escherichia coli*: Studies on Iron-Sulfur Cluster Implementation and Catalysis," *J. Am. Chem. Soc.* 126(40):12847-12855.

Greenberg, J.P. et al. (1993). "Sub-Parts Per Billion Detection of Isoprene Using a Reduction Gas Detector with a Portable Gas Chromatograph," *Atmospheric Environment* 27A(16):2689-2692.

Guzman, L.M. et al. (Jul. 1995). "Tight Regulation, Modulation, and High-Level Expression by Vectors Containing the Arabinsoe PBAD Promoter," *Journal of Bacteriology* 177(14):4121-4130.

Harkki, A. et al. (Jun. 1989). "A Novel Fungal Expression System: Secretion of Active Calf Chymosin from the Filamentous Fungus *Trichoderma reesei*," *Bio/Technology* 7:596-603.

Harkki, A. et al. (Mar. 1991). "Genetic Engineering of *Trichoderma* to Produce Strains with Novel Cellulase Profiles," *Enzyme Microb. Technol.* 13:227-233.

Hedl, M. et al. (Apr. 2002). "*Enterococcus faecalis* Acetoacetyl-Coenzyme A Thiolase/3-Hydroxy-3-Methyglutaryl-Coenzyme A Reductase, a Dual-Function Protein of Isopentenyl Diphosphate Biosynthesis," *J. Bacteriol.* 184(8):2116-2122.

Hoeffler, J-F. et al. (Sep. 2002). "Isoprenoid Biosynthesis Via the Methylerythritol Phosphate Pathway. Mechanistic Investigations of the 1-deoxy-D-xylulose 5-phosphate Reductoisomerase," *Eur. J. Biochem.* 269(18):4446-4457.

Hunter, B.K. (1985). "Formaldehyde Metabolism by *Escherichia coli*. Carbon and Solvent Deuterium Incorporation into Glycerol, 1,2-Propanediol, and 1,3-Propanediol," *Biochemistry* 24(15):4148-4155.

Ilmén, M. et al. (Apr. 1997). "Regulation of Cellulase Gene Expression in the Filamentous Fungus *Trichoderma reesei*," *Appl. Environ. Microbiol.* 63(4):1298-1306.

Innis, M.A. et al. (Apr. 1985). "Expression, Glycosylation, and Secretion of an *Aspergillus* Glucoamylase by *Saccharomyces cerevisiae*," *Science* 228:21-26.

International Search Report mailed on Sep. 9, 2010, for PCT Patent Application No. PCT/US2010/038904, filed Jun. 16, 2010, published on Dec. 23, 2010, as WO 2010/148150, 3 pages.

International Search Report mailed on Mar. 2, 2012, for PCT Patent Application No. PCT/US2011/066924, filed on Dec. 22, 2011, published on Jun. 28, 2012 as WO 2012/088450, 3 pages.

International Search Report mailed on May 18, 2012, for PCT Patent Application No. PCT/US2011/066949, filed on Dec. 22, 2011, published on Jun. 28, 2012, as WO 2012/088462, 3 pages.

Iwakura, M. et al. (1979). "Studies on Regulatory Functions of Malic Enzymes," *J. Biochem.* 85:1355-1365.

Jawaid, S. et al. (Dec. 14, 2009). "Kinetic Characterization and Phosphoregulation of the *Francisella tularensis* 1-Deoxy-D-Xylulose 5-Phosphate Reductoisomerase (MEP Synthase)," *PLoS ONE* 4(12):e8288, 9 pages.

Jobling, M.G. et al. (Jul. 17, 1990). "Construction of Vectors with the p15a Replicon, Kanamycin Resistance, Inducible *lacZα* and pUC18 or pUC19 Multiple Cloning Sites," *Nucleic Acids Research* 18(17):5315-5316.

Julsing, M.K. et al. (Jul. 2007, e-pub Apr. 26, 2007) "Functional Analysis of Genes Involved in the Biosynthesis of Isoprene in *Bacillus subtilis*," *Appl. Microbiol. Biotechnol.* 75(6):1377-1384.

Justino, M.C. et al. (Apr. 6, 2007). "*Escherichia coli* Di-iron YtfE Protein Is Necessary for the Repair of Stress-damaged Iron-Sulfur Clusters," *The Journal of Biological Chemistry* 282(14):10352-10359.

Justino, M.C. et al. (2009) "Di-iron Proteins of the Ric Family are Involved in Iron-sulfur Cluster Repair," *Biometals* 22:99-108.

Kajiwara, S. et al. (1997). "Expression of an Exogenous Isopentenyl Diphosphate Isomerase Gene Enhances Isoprenoid Biosynthesis in *Escherichia coli*," *Biochem. J.* 324:421-426.

Kajiwara, Y. et al. (1997). "Production of Acid-Stable α-Amylase by *Aspergillus kawachii* During Barley Shochu-Koji Production," *Journal of Fermentation and Bioengineering* 84(3):224-227.

Kakuda, H. et al. (Jun. 13, 1994). "Identification and Characterization of the *ackA* (Acetate Kinase A)-*pta* (Phosphotransacetylase) Operon and Complementation Analysis of Acetate Utilization by an *ackA-pta* Deletion Mutant of *Escherichia coli*," J. Biochem. 116:916-922.

Kelley, J.M. et al. (1985). "Transformation of *Aspergillus niger* by the *amdS* Gene of *Aspergillus nidulans*," *The EMBO Journal* 4(2):475-479.

Kimchi-Sarfaty, C. et al. (Jan. 26, 2007). "A 'Silent' Polymorphism in the *MDR1* Gene Changes Substrate Specificity," *Science* 315:525-528.

Kisselev, L. (Jan. 2002). "Polypeptide Release Factors in Prokaryotes and Eukaryotes: Same Function, Different Structure," *Structure* 10:8-9.

Koppisch, A.T. et al. (2002). "*E. coli* MEP Synthase: Steady-State Kinetic Analysis and Substrate Binding," *Biochemistry* 41:236-243.

Kovach, M.E. et al. (1995). "Four New Derivatives of the Broad-Host-Range Cloning Vector pBBR1MCS, Carrying Different Antibiotic-Resistance Cassettes," *Gene* 166:175-176.

Leonardi, R. et al. (2003, e-pub. Mar. 5, 2003). "Thiamine Biosynthesis in *Escherichia coli*: Isolation and Initial Characterisation of the ThiGH Complex," *FEBS Letters* 539(1-3):95-99.

Leonardi, R. et al. (Apr. 23, 2004). "Thiamine Biosynthesis in *Escherichia coli*. In Vitro Reconstitution of the Thiazole Synthase Activity," *J. Biol. Chem.* 279(17):17054-17062.

Lerner, C.G. et al. (1990). "Low Copy Number Plasmids for Regulated Low-Level Expression of Cloned Genes in *Escherichia coli* with Blue/White Insert Screening Capability," *Nucleic Acids Research* 18(15):4631.

Lindberg, P. et al. (Jan. 2010). "Engineering a Platform for Photosynthetic Isoprene Production in Cyanobacteria, Using *Synechocystis* as the Model Organism," *Metabolic Engineering* 12(1):70-79.

Loiseau, L. et al. (Aug. 21, 2007). "ErpA, an Iron-Sulfur (Fe—S) Protein of the A-type Essential for Respiratory Metabolism in *Escherichia coli*," *PNAS* 104(34):13626-13631.

Lüttgen, H. et al. (Feb. 1, 2000). "Biosynthesis of Terpenoids: YchB Protein of *Escherichia coli* Phosphorylates the 2-hydroxy Group of 4-diphosphocytidyl-2C-methyl-D-erythritol," *PNAS* 97(3):1062-1067.

Lynch, M.D. et al. (Jan. 2007). "SCALEs: Multiscale Analysis of Library Enrichment," *Nature Methods* 4(1):87-93.

Martin, V. et al. (Jul. 2003). "Engineering a Mevalonate Pathway in *Escherichia coli* for Production of Terpenoids," *Nature Biotechnology* 21(7):796-802.

Maurus, R. et al. (2003). "Insights into the Evolution of Allosteric Properties. The NADH Binding Site of Hexameric Type II Citrate Synthases," *Biochemistry* 42:5555-5565.

Miller, B. et al. (Jul. 2001, e-pub. May 10, 2001). "First Isolation of an Isoprene Synthase Gene from Poplar and Successful Expression of the Gene in *Escherichia coli*," *Planta.* 213(3):483-487.

Nackley, A.G. et al. (Dec. 22, 2006). "Human Caechol-*O*-Methyltransferase Haplotypes Modulate Protein Expression by Altering mRNA Secondary Structure," *Science* 314:1930-1933.

NCBI. (2012). Located at <http://www.ncbi.nlm.nih.gov/> last visited on May 29, 2012, two pages.

Nemeria, N. et al. (Jun. 3, 2005). "Glutamate 636 of the *Escherichia coli* Pyruvate Dehydrogenase-E1 Participates in Active Center Communication and Behaves as an Engineered Acetolactate Synthase With Unusual Stereoselectivity," *J. Biol. Chem.* 280(22):21473-21482.

Ner, S.S. et al. (Nov. 8, 1983). "Complete Sequence of the *glt* A Gene Encoding Citrate Synthase in *Escherichia coli*," *Biochemistry* 22(23):5243-5249.

Nevalainen, K.M.H. et al. (1992). "The Molecular Biology of *Trichoderma* and Its Application to the Expression of Both Homologous and Heterologous Genes," Chapter 6 in *Molecular Industrial Mycology, Systems and Applications for Filamentous Fungi*, Leong, S.A. et al. eds., Marcel Dekker Inc.: New York, NY, pp. 129-148.

(56) References Cited

OTHER PUBLICATIONS

Nunberg, J.H. et al. (Nov. 1984). "Molecular Cloning and Characterization of the Glucoamylase Gene of *Aspergillus awamori*," *Mol. Cell. Biol.* 4(11):2306-2315.

Ogasawara, H. et al. (Aug. 2007). "PdhR (Pyruvate Dehydrogenase Complex Regulator) Controls the Respiratory Electron Transport System in *Escherichia coli*," *Journal of Bacteriology* 189(15):5534-5541.

Oh, M-K. et al. (Apr. 12, 2002). "Global Expression Profiling of Acetate-grown *Escherichia coli*," *J. Biol. Chem.* 277(15):13175-13183.

Okada, K. et al. (May 27, 2005). "Cyanobacterial Non-mevalonate Pathway. (E)-4-Hydroxy-3-Methylbut-2-Enyl Diphosphate Synthase Interacts with Ferredoxin in *Thermosynechococcus elongatus* BP-1," *J. Biol. Chem.* 280(21):20672-20679.

Oulmouden, A. et al. (1991). "Nucleotide Sequence of the *ERG12* Gene of *Saccharomyces cerevisiae* Encoding Mevalonate Kinase," *Curr. Genet.* 19:9-14.

Palmeros, B. et al. (2000). "A Family of Removable Cassettes Designed to Obtain Antibiotic-Resistance-Free Genomic Modifications of *Escherichia coli* and Other Bacteria," *Gene* 247(1-2):255-264.

Penttila, M. et al. (1987). "A Versatile Transformation System for the Cellulolytic Filamentous Fungus *Trichoderma reesei*," *Gene* 61:155-164.

Perrenoud, A. et al. (May 2005). "Impact of Global Transcriptional Regulation by ArcA, ArcB, Cra, Crp, Cya, Fnr, and Mlc on Glucose Catabolism in *Escherichia coli*," *Journal of Bacteriology* 187(9):3171-3179.

Pourquié, J. et al. (1988). "Scale Up of Cellulase Production and Utilization," in *Biochemistry and Genetics of Cellulose Degradation*, Aubert, J-P. et al. eds., Academic Press: San Diego, CA, pp. 71-86.

Puan, K-J. et al. (2005). "*fldA* is an Essential Gene Required in the 2-C-methyl-D-erythritol 4-phosphate Pathway for Isoprenoid Biosynthesis," *FEBS Letters* 579:3802-3806.

Rohdich, F. et al. (Oct. 12, 1999). "Cytidine 5'-triphosphate-dependent Biosynthesis of Isoprenoids: YgbP Protein of *Escherichia coli* Catalyzes the Formation of 4-Diphosphocytidyl-2-C-methylerythritol," *PNAS* 96(21):11758-11763.

Rohdich, F. et al. (Jun. 6, 2000). "Biosynthesis of Terpenoids: 4-Diphosphocytidyl-2C-methyl-D-erythritol Synthase of *Arabidopsis thaliana*," *PNAS* 97(12):6451-6456.

Romanos, M.A. et al. (Jun. 1992). "Foreign Gene Expression in Yeast: a Review," *Yeast* 8(6):423-488.

Sakamoto, I, et al. (2000), "Synthesis of 2-C-Methyl-D-erythritol and 2-C-Methyl-L-threitol; Determination of the Absolute Configuration of 2-C-Methyl-1,2,3,4-butanetetrol Isolated from *Phlox sublata* L," *Biosci. Biotechnol. Biochem.* 64(9):1915-1922.

Sánchez, A.M. et al. (May 2005). "Novel Pathway Engineering Design of the Anaerobic Central Metabolic Pathway in *Escherichia coli* to Increase Succinate Yield and Productivity," *Metabolic Engineering* 7(3):229-239.

Sangari, F.J. et al. (Aug. 10, 2010). "A New Family of Enzymes Catalyzing the First Committed Step of the Methylerythritol 4-phosphate (MEP) Pathway for Isoprenoid Biosynthesis in Bacteria," *PNAS* 107(32):14081-14086.

Sasaki, K. et al. (2005, e-pub. Apr. 7, 2005). "Gene Expression and Characterization of Isoprene Synthase from *Populus alba*," *FEBS Letters* 579(11):2514-2518.

Sauna, Z.E. et al. (2007, e-pub. Oct. 17, 2007). "Silent Polymorphisms Speak: How They Affect Pharmacogenomics and the Treatment of Cancer," *Cancer Res.* 67(20):9609-9612.

Sauret-Güeto, S. et al. (2006, e-pub. Jan. 9, 2006). "A Mutant Pyruvate Dehydrogenase E1 Subunit Allows Survival of *Escherichia coli* Strains Defective in 1-deoxy-D-xylulose 5-phosphate Synthase," *FEBS Letters* 580:736-740.

Schnitzler, J-P. et al. (2005, e-pub. Jul. 29, 2005). "Biochemical Properties of Isoprene Synthase in Poplar (*Populus x canescens*)," *Planta* 222(5):777-786.

Schwartz. C.J. et al. (Dec. 18, 2001). "IscR, an Fe—S Cluster-Containing Transcription Factor, Represses Expression of *Escherichia coli* Genes Encoding Fe-S Cluster Assembly Proteins," *PNAS*, 98(26):14895-14900.

Seemann, M. et al. (Nov. 15, 2002). "Isoprenoid Biosynthesis Through the Methylerythritol Phosphate Pathway: The (E)-4-Hydroxy-3-methylbut-2-enyl Diphosphate Synthase (GcpE) is a [4Fe—4S] Protein," *Angew. Chem, Int. Ed.* 41(22):4337-4339.

Seemann, M. et al. (2006, e-pub. Feb. 2, 2006). "Isoprenoid Biosynthesis in Plant Chloroplasts Via the MEP Pathway: Direct Thylakoid/Ferredoxin-Dependent Photoreduction of GcpE/IspG," *FEBS Letters* 580(6):1547-1552.

Seffernick, J.L. et al. (Apr. 2001). "Melamine Deaminase and Atrazine Chlorohydrolase: 98 Percent Identical but Functionally Different," *J. Bacteriol.* 183(8):2405-2410.

Sen, S. et al. (2007). "Developments in Directed Evolution for Improving Enzyme Functions," *Appl. Biochem. Biotechnol.* 143:212-223.

Seta, F.D. et al. (Aug. 1997). "Characterization of *Escherichia coli* Strains With *gapA* and *gapB* Genes Deleted," *Journal of Bacteriology*, 179(16):5218-5221.

Sharkey, T.D. et al. (Feb. 2005). "Evolution of the Isoprene Biosynthetic Pathway in Kudzu," *Plant Physiology* 137:700-712.

Sheir-Neiss, G. et al. (Jul. 1984). "Characterization of the Secreted Cellulases of *Trichoderma reesei* Wild Type and Mutants During Controlled Fermentations," *Appl. Microbiol. Biotechnol.* 20(1):46-53.

Shimizu, M. et al. (1969) "Phosphotransacetylase of *Escherichia coli* B, Purification and Properties," *Biochim. Biophys. Acta.* 191(3):550-558.

Silver, G.M. et al. (1991). "Enzymatic Synthesis of Isoprene from Dimethylallyl Diphosphate in Aspen Leaf Extracts," *Plant Physiol.* 97:1588-1591.

Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.

Sivy, T.L. et al. (May 31, 2002). "Isoprene Synthase Activity Parallels Fluctuations of Isoprene Release During Growth of *Bacillus subtilis*," *Biochem. Biophys. Res. Commun.* 294(1):71-75.

Sprenger, G.A. et al. (Nov. 1997). "Identification of a Thiamin-Dependent Synthase in *Escherichia coli* Required for the Formation of the 1-deoxy-D-xylulose 5-phosphate Precursor to Isoprenoids, Thiamin, and Pyridoxol," *PNAS* 94:12857-12862.

Stokell, D.J. et al. (Sep. 12, 2003). "Probing the Roles of Key Residues in the Unique Regulatory NADH Binding Site of Type II Citrate Synthase of *Escherichia coli*," *J. Biol. Chem.* 278(37):35435-35443.

Sulter, G.J. et al. (1990). "Proliferation and Metabolic Significance of Peroxisomes in *Candida boidinii* During Growth on $_D$-alanine or Oleic Acid as the Sole Carbon Source," *Arch. Microbiol.* 153:485-489.

Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *J. Bacteriol.* 184(15):4065-4070.

Swiss Institute of Bioinformatics (2012). "ExPASy Bioinformatics Resource Portal," located at <http://expasy.org>, last visited on Dec. 27, 2012, 1 page.

Tchieu, J.H. et al. (Jul. 2001). "The Complete Phosphotransferase System in *Escherichia coli*," *J. Mol. Microbiol. Biotechnol.* 3(3):329-346.

Teymouri, F. et al. (2005, e-pub. Feb. 24, 2005). "Optimization of the Ammonia Fiber Explosion (AFEX) Treatment Parameters for Enzymatic Hydrolysis of Corn Stover," *Bioresource Technology* 96:2014-2018.

Thomason, L.C. et al. (Dec. 2004). "Identification of the *Escherichia coli* K-12 *ybhE* Gene as *pgl*, Encoding 6-Phosphogluconolactonase," *Journal of Bacteriology*, 186(24):8248-8253.

Tokumoto, U. et al. (2001). "Genetic Analysis of the isc Operon in *Escherichia coli* Involved in the Biogenesis of Cellular Iron-Sulfur Proteins," *J Biochem.* 130(1):63-71.

Tsay, Y.H. et al. (Feb. 1991). "Cloning and Characterization of *ERG8*, an Essential Gene of *Saccharomyces cerevisiae* That Encodes Phosphomevalonate Kinase," *Mol. Cell. Biol.* 11(2):620-631.

(56) References Cited

OTHER PUBLICATIONS

U.S. Appl. No. 13/283,564, filed Oct. 27, 2011 by Beck et al.
Underwood, S.A. et al. (Mar. 2002). "Flux through Citrate Synthase Limits the Growth of Ethanologenic *Escherichia coli* KO11 during Xylose Fermentation," *Applied and Environmental Microbiology* 68(3):1071-1081.
Van Den Hondel, C.A.M.J.J. et al. (1991). "Heterologous Gene Expression in Filamentous Fungi," Chapter 18 in *More Gene Manipulations in Fungi*, Bennet, J.W. et al. eds., Academic Press, Inc.: San Diego, CA, pp. 396-428.
Vander Horn, P.B. et al. (Feb. 1993). "Structural Genes for Thiamine Biosynthetic Enzymes (*thiCEFGH*) in *Escherichia coli* K-12," *J. Bacteriol.* 175(4):982-992.
Vinella, D. et al. (May 29, 2009). "Iron—Sulfur (Fe/S) Protein Biogenesis: Phylogenomic and Genetic Studies of A-Type Carriers," *PLOS Genetics* 5(5):1-16 of e1000497.
Wagner, W.P. et al. (Jan. 2000). "Isoprene Biosynthesis in *Bacillus subtilis* via the Methylerythritol Phosphate Pathway," *J. Nat. Prod.* 63(1):37-40.
Ward, M. et al. (Aug. 1993). "Use of *Aspergillus* Overproducing Mutants, Cured for Integrated Plasmid, to Overproduce Heterologous Proteins," *Appl. Microbiol. Biotechnol.* 39(6):738-743.
Whisstock, J.C. et al. (2003). "Prediction of Protein Function from Protein Sequence and Structure," *Quarterly Reviews of Biophysics* 36(3):307-340.
Wiegand, G. et al. (1986). "Citrate Synthase: Structure, Control, and Mechanism," *Ann. Rev. Biophys. Biophys. Chem.* 15:97-117.
Wishart, M. J. et al. (Nov. 10, 1995). "A Single Mutation Converts a Novel Phosphotyrosine Binding Domain into a Dual-Specificity Phosphatase," *J. Biol. Chem.* 270(45):26782-26785.
Withers, S.T. et al. (Oct. 2007). "Identification of Isopentenol Biosynthetic Genes from *Bacillus subtilis* by a Screening Method Based on Isoprenoid Precursor Toxicity," *Applied and Environmental Microbiology* 73(19):6277-6283.

Witkowski, A. et al. (1999). "Conversion of $\beta$-Ketoacyl Synthase to a Malonyl Decarboxylase by Replacement of the Active-Site Cysteine with Glutamine," *Biochemistry* 38:11643-11650.
Wolfe, A. (Mar. 2005). "The Acetate Switch," *Microbiology and Molecular Biology Reviews* 69(1):12-50.
Wolff, M. et al. (2003). "Isoprenoid Biosynthesis via the Methylerythritol Phosphate Pathway: The (*E*)-4-hydroxy-3-methylbut-2-enyl Diphosphate Reductase (LytB/IspH) from *Escherichia coli* is a [4Fe—4S] Protein," *FEBS Letters* 541:115-120.
Yamada, K. et al. (1989). "Production of Glycerol from Methanol by a Mutant Strain of *Candida boidinii* No. 2201," *Agric. Biol. Chem.* 53(2):541-543.
Yelton, M.M. et al. (Mar. 1984). "Transformation of *Aspergillus nidulans* by Using a *trpC* Plasmid," *PNAS* 81:1470-1474.
Zepeck, F. et al. (Nov. 11, 2005). "Biosynthesis of Isoprenoids. Purification and Properties of IspG Protein from *Escherichia coli*," *J. Org. Chem.* 70(23):9168-9174.
Miller, B. (2001). "Erstmalige Isolierung eines Isoprensynthase-Gens and heterologe Expression des aus der Pappel stammenden Gens sowie Charakterisierung der Eingangsgene des Mevalonat-unabhängigen Isoprenoidbiosyntheseweges aus dem Cyanobakterium Synechococcus leopoliensis," located at <http://kups.ub.uni-koeln.de/volltexte/2003/883/pdf/millerbarbara.pdf>, last visited on Feb. 25, 2013, two pages (with English Translation).
Rodríguez-Concepción, M. et al. (Nov. 2002). "Elucidation of the Methylerythritol Phosphate Pathway for Isoprenoid Biosynthesis in Bacteria and Plastids. A Metabolic Milestone Achieved Through Genomics," *Plant Physiology* 130:1079-1089.
Singh, N. et al. (2007). "Targeting the Methyl Erythritol Phosphate (MEP) Pathway for Novel Antimalarial, Antibacterial and Herbicidal Drug Discovery: Inhibition of 1-Deoxy-D-Xylulose-5-Phosphate Reductoisomerase (DXR) Enzyme," *Current Pharmaceutical Design* 13(11):1161-1177.

\* cited by examiner

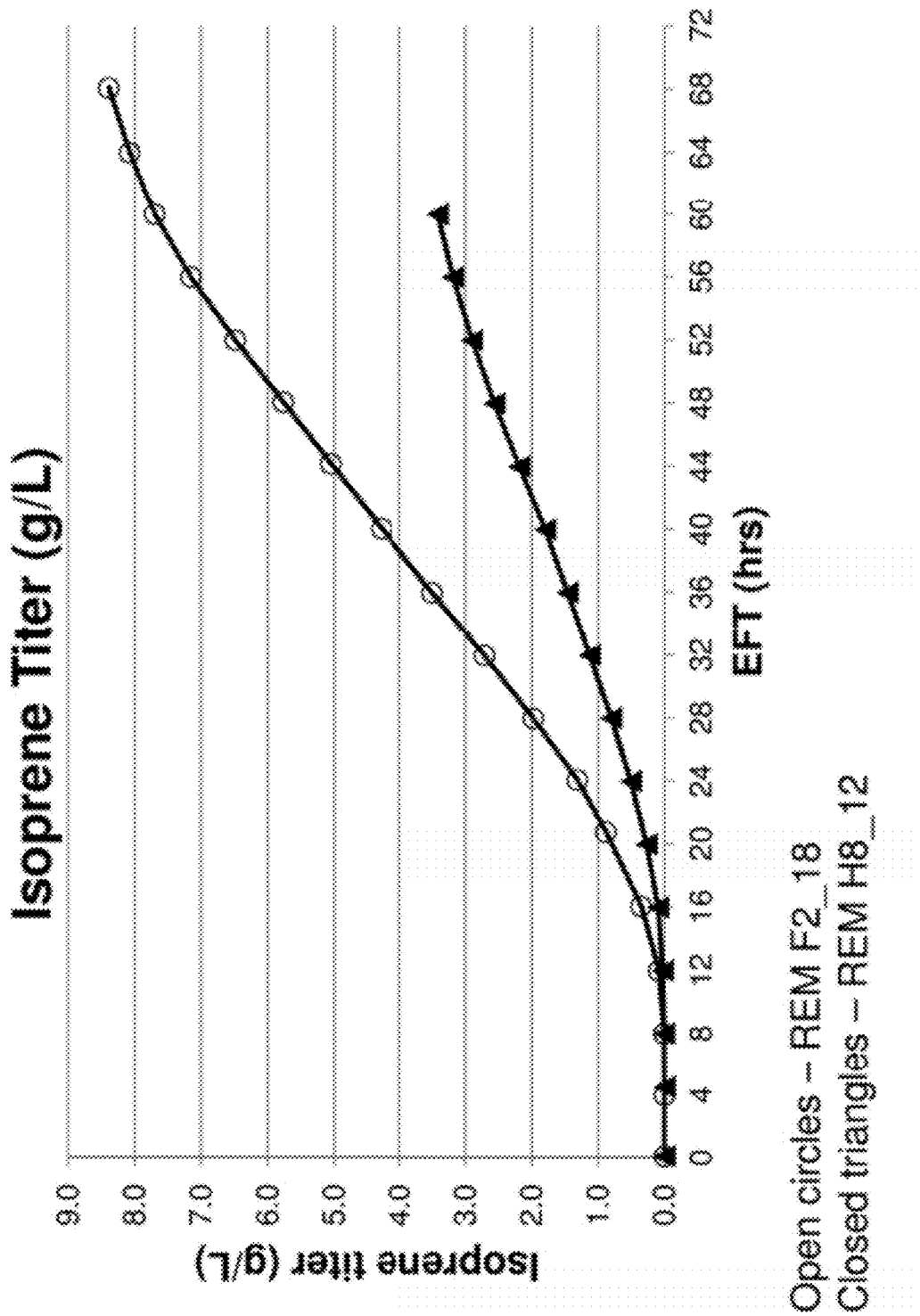

COMPOSITIONS AND METHODS FOR IMPROVED ISOPRENE PRODUCTION USING TWO TYPES OF ISPG ENZYMES

CROSS-REFERENCE TO RELATED APPLICATIONS

This application claims priority benefit of U.S. provisional patent application No. 61/426,505, filed on Dec. 22, 2010, the content of which is hereby incorporated by reference herein in its entirety.

FIELD OF THE INVENTION

The present invention relates generally to compositions and methods for improving the production of isoprene from recombinant cells by utilizing two types of IspG enzymes.

BACKGROUND OF THE INVENTION

Isoprene (2-methyl-1,3-butadiene) is the critical starting material for a variety of synthetic polymers, most notably synthetic rubbers. Isoprene is naturally produced by a variety of microbial, plant, and animal species. In particular, two pathways have been identified for the biosynthesis of isoprene: the mevalonate (MVA) pathway and the non-mevalonate (DXP) pathway. However, the yield of isoprene from naturally-occurring organisms is commercially unattractive. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex.

Currently, the tire and rubber industry is based on the use of natural and synthetic rubber. Natural rubber is obtained from the milky juice of rubber trees or plants found in the rainforests of Africa. Synthetic rubber is based primarily on butadiene polymers. For these polymers, butadiene is obtained as a co-product from ethylene and propylene manufacture.

While isoprene can be obtained by fractionating petroleum, the purification of this material is expensive and time-consuming. Petroleum cracking of the C5 stream of hydrocarbons produces only about 15% isoprene. Thus, more economical methods for producing isoprene are needed. In particular, methods that produce isoprene at rates, titers, and purity that are sufficient to meet the demands of a robust commercial process are desirable. Also desired are systems for producing isoprene from inexpensive starting materials. The invention described herein addresses these needs and provides additional benefits as well.

All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention.

BRIEF SUMMARY OF THE INVENTION

The invention provides, inter alia, compositions and methods for the production of isoprene in increased amounts using two types of 1-hydroxy-2-methyl-2-(E)-butenyl 4-diphosphate synthase (HDS or IspG) IspG enzymes and/or other DXP pathway nucleic acids and polypeptides, iron-sulfur cluster-interacting redox nucleic acids and polypeptides, and isoprene synthase nucleic acids and polypeptides.

In one aspect, the invention provides for recombinant cells capable of producing isoprene, the cell comprising (i) a heterologous nucleic acid encoding a first 1-hydroxy-2-methyl-2-(E)-butenyl 4-diphosphate synthase (IspG) polypeptide, or one or more copies of an endogenous nucleic acid encoding an IspG polypeptide, of a first species; (ii) a heterologous nucleic acid encoding a second IspG polypeptide, or one or more copies of an endogenous nucleic acid encoding an IspG polypeptide, of a second species, wherein the second species differs from the first species; (iii) a heterologous nucleic acid encoding at least one additional DXP pathway enzyme; and (iv) a nucleic acid encoding isoprene synthase polypeptide. In another aspect, the invention provides for recombinant cells capable of producing isoprene, the cell transformed with: (i) a nucleic acid encoding a first 1-hydroxy-2-methyl-2-(E)-butenyl 4-diphosphate synthase (IspG) polypeptide of a first species; (ii) a nucleic acid encoding a second IspG polypeptide of a second species, wherein the second species differs from the first species; (iii) a nucleic acid encoding at least one DXP pathway enzyme and (iv) a nucleic acid encoding an isoprene synthase polypeptide. In any of these aspects, the first IspG is from *T. longatus*. In other aspects, the second IspG is from *E. coli*. In some aspects, the additional DXP pathway enzyme is selected from the group of DXS, DXR, MCT, CMK, MCS, HDR (IspH), and IDI. In some aspects, the additional DXP pathway enzyme can be any one or more of: DXS, DXR, HDR (IspH), and IDI.

In any of the aspects herein, the recombinant cell further comprises a heterologous nucleic acid encoding an iron-sulfur cluster-interacting redox polypeptide or one or more copies of an endogenous nucleic acid encoding an iron-sulfur cluster-interacting redox polypeptide. In some aspects, the iron-sulfur cluster-interacting redox polypeptides are selected from ferredoxons and flavodoxins.

In any of the aspects herein, the recombinant cell further comprises a heterologous nucleic acid encoding a DXP pathway associated polypeptides (e.g., DXP partner proteins) or one or more copies of an endogenous nucleic acid encoding a DXP pathway associated polypeptides (e.g., DXP partner proteins). In certain aspects, the DXP pathway associated polypeptides are selected from chaperonins, included among which are enzymes exhibiting the well known protein-folding and/or re-folding functions as well as enzymes involved in the delivery, maintenance, and/or repair of functional iron-sulfur clusters.

In any of the aspects herein, the recombinant cell further comprises one or more heterologous nucleic acid encoding an isopentenyl-diphosphate delta-isomerase (IDI) polypeptide or one or more copies of an endogenous nucleic acid encoding an IDI polypeptide.

In any of the aspects herein, the recombinant cell further comprises one or more heterologous nucleic acid encoding a MVA pathway polypeptide or one or more copies of an endogenous nucleic acid encoding a MVA pathway polypeptide.

In any of the aspects herein, the isoprene synthase polypeptide is a plant isoprene synthase polypeptide. In any of the aspects herein, the isoprene synthase polypeptide is *P. alba* isoprene synthase. In some aspects, the isoprene synthase polypeptide is a polypeptide from *Pueraria* or *Populus* or a hybrid, *Populus alba* x *Populus tremula*. In other aspects, the isoprene synthase polypeptide is selected from the group consisting of *Pueraria montana* or *Pueraria lobata, Populus tremuloides, Populus alba, Populus nigra*, and *Populus trichocarpa*. In other aspects, the plant isoprene synthase polypeptide is a kudzu isoprene synthase polypeptide. In some aspects, the isoprene synthase polypeptide is a naturally-occurring isoprene synthase polypeptide. In other aspects, the isoprene synthase polypeptide is a non-naturally-occurring isoprene synthase polypeptide. In other aspects, the isoprene synthase polypeptide is an isoprene synthase variant or isoprene synthase mutant as disclosed in WO 2009/041581, US Publ. No. 2010/0003716, WO 2010/0124146 or US Appl. 13/283,564.

In any of the aspects herein, the recombinant cell is a bacterial, algal, fungal or yeast cell In some aspects, the recombinant cell is a bacterial cell. In some aspects, the bacterial cell is a gram-positive bacterial cell or gram-negative bacterial cell. In some aspects, the bacterial cell is *E. coli*. In other aspects, the bacterial cell is selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells. In any of the aspects herein, the nucleic acids can be on one or multiple plasmids.

In another aspect, the invention also provides for a cell culture comprising any of the recombinant cells disclosed herein, wherein the cell culture is capable of producing at least about 8.4 g/l of isoprene.

In another aspect, the invention also provides for methods of producing isoprene, the method comprising: (a) culturing any of the recombinant cells disclosed herein under conditions suitable for producing isoprene and (b) producing isoprene. In some aspects, the method further comprises recovering the isoprene. In other aspects, the recombinant cells produce greater than about 8.4 g/l of isoprene.

BRIEF DESCRIPTION OF THE DRAWINGS

FIG. 4 shows a graph of isoprene titer versus time in individual 15 L scale fermentations of REM F2__18 and REM H8-12.

DETAILED DESCRIPTION OF THE INVENTION

Figure 1:
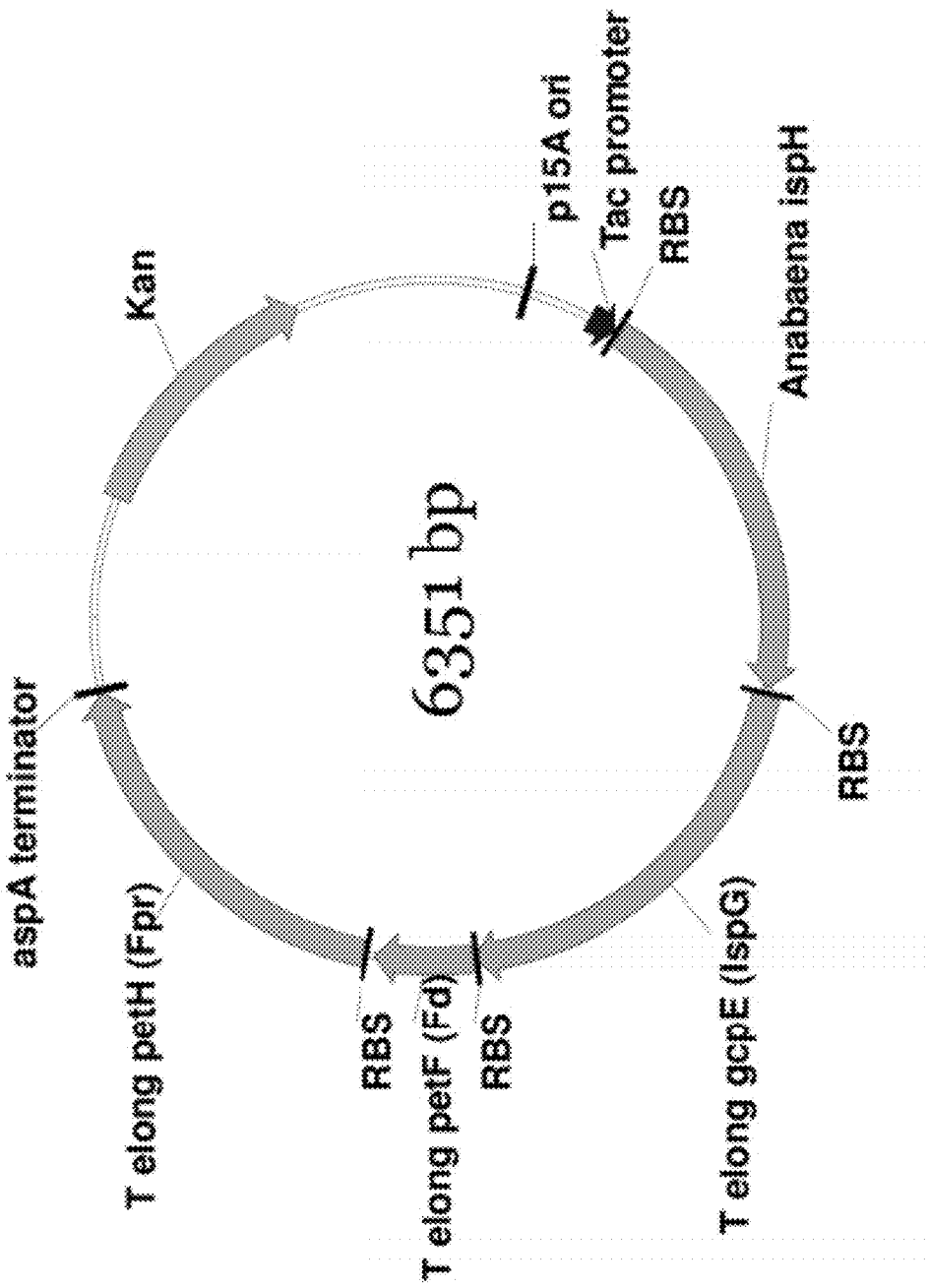
FIG. 1 depicts a plasmid map of Ptac Anabaena ispH-T elong ispG system aspA term/pEWL454. kan—kanamycin antibiotic resistance marker; p15A ori—plasmid origin of replication; RBS—ribosome binding site. The positions of the Tac promoter, aspA terminator, and genes encoding the IspH and IspG system components are indicated on the map; Anabaena ispH encodes 4-hydroxy-3-methylbut-2-enyl diphosphate reductase (IspH), T elong gcpE encodes 1-hydroxy-2-methyl-2-(E)-butenyl 4-diphosphate synthase (IspG), T elong petF encodes ferredoxin (Fd), and T elong petH encodes ferredoxin-NADP$^+$ oxidoreductase (Fpr).

The invention provides, inter alia, systems, compositions and methods for the increased production of isoprene by engineering recombinant cells with two types of IspG enzymes, a DXP pathway enzyme, and an isoprene synthase polypeptide such that increased amounts of isoprene can be produced.

DEFINITIONS

Unless defined otherwise, the meanings of all technical and scientific terms used herein are those commonly understood by one of skill in the art to which this invention belongs. Singleton, et al., Dictionary of Microbiology and Molecular Biology, 2nd ed., John Wiley and Sons, New York (1994), and Hale & Marham, The Harper Collins Dictionary of Biology, Harper Perennial, N.Y. (1991) provide one of skill with a general dictionary of many of the terms used in this invention. It is to be understood that this invention is not limited to the particular methodology, protocols, and reagents described, as these may vary. One of skill in the art will also appreciate that any methods and materials similar or equivalent to those described herein can also be used to practice or test the invention. The headings provided herein are not limitations of the various aspects or aspects of the invention which can be had by reference to the specification as a whole.

As used herein, the term "isoprene" or "2-methyl-1,3-butadiene" (CAS#78-79-5) refers to the direct and final volatile C5 hydrocarbon product from the elimination of pyrophosphate from 3,3-dimethylallyl pyrophosphate (DMAPP), and does not involve the linking or polymerization of one or more isopentenyl diphosphate (IPP) molecules to one or more DMAPP molecules. The term "isoprene" is not generally intended to be limited to its method of production.

As used herein, the term "polypeptides" includes polypeptides, proteins, peptides, fragments of polypeptides, and fusion polypeptides.

As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide. An isolated polypeptide can be a non-naturally occurring polypeptide.

By "heterologous polypeptide" is meant a polypeptide encoded by a nucleic acid sequence derived from a different organism, species, or strain than the host cell. In some aspects, a heterologous polypeptide is not identical to a wild-type polypeptide that is found in the same host cell in nature.

As used herein, a "nucleic acid" refers to two or more deoxyribonucleotides and/or ribonucleotides covalently joined together in either single or double-stranded form.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. In some cases, a recombinant nucleic acid is a nucleic acid that encodes a non-naturally occurring polypeptide.

By "heterologous nucleic acid" is meant a nucleic acid sequence derived from a different organism, species or strain than the host cell. In some aspects, the heterologous nucleic acid is not identical to a wild-type nucleic acid that is found in the same host cell in nature.

As used herein, the phrase, "various nucleic acids and polypeptides associated with the DXP pathway," or "DXP pathway associated nucleic acid(s) or polypeptide(s)" refers to any nucleic acid or polypeptide that interacts with DXP pathway polypeptides or nucleic acids, including, but not limited to, a terpene synthase (e.g., ocimene synthase, farnesene synthase, and artemesinin synthase), either directly or indirectly.

For use herein, unless clearly indicated otherwise, use of the terms "a", "an," and the like refers to one or more.

Reference to "about" a value or parameter herein includes (and describes) aspects that are directed to that value or parameter per se. For example, description referring to "about X" includes description of "X." Numeric ranges are inclusive of the numbers defining the range.

It is understood that aspects and aspects of the invention described herein include "comprising," "consisting," and "consisting essentially of" aspects and aspects.

Recombinant Cells Capable of Producing Isoprene

As described in greater detail and further exemplified herein, recombinant cells capable of producing isoprene can be engineered for increased isoprene production. As described herein, increased isoprene production can be achieved by recombinant cells capable of producing isoprene comprising (i) a heterologous nucleic acid encoding a first 1-hydroxy-2-methyl-2-(E)-butenyl 4-diphosphate synthase (IspG) polypeptide, or one or more copies of an endogenous nucleic acid encoding an IspG polypeptide, of a first species; (ii) a heterologous nucleic acid encoding a second IspG polypeptide, or one or more copies of an endogenous nucleic acid encoding an IspG polypeptide, of a second species, wherein the second species differs from the first species; (iii) a heterologous nucleic acid encoding at least one additional DXP pathway enzyme; and (iv) a nucleic acid encoding isoprene synthase polypeptide. In one aspect, the first IspG polypeptide of a first species is from *E. coli*. In another aspect, the second IspG polypeptide of a second species is from *T. elongatus* IspG.

IspG Enzymes and Systems

IspG enzymes are part of the lower DXP pathway. IspG nucleic acids code for 1-hydroxy-2-methyl-2-(E)-butenyl 4-diphosphate synthase (IspG) or HDS polypeptides, which convert 2-C-methyl-D-erythritol 2,4-cyclodiphoshpate (ME-CPP or cMEPP) into (E)-4-hydroxy-3-methylbut-2-en-1-yl-diphosphate (HMBPP or HDMAPP).

Some recombinant cells (e.g., BL21 *E. coli* strain) that have been engineered to utilize the DXP pathway for isoprenoid biosynthesis have IspG activity that is too low to support high yield generation of isoprene from glucose. Thus for commercial production of isoprene, these recombinant cells are not sufficient for generating the commercially relevant levels of isoprene that are needed. Accordingly, the invention provides for compositions and methods for increasing isoprene production by increasing IspG polypeptide activity.

For increasing IspG polypeptide activity, one option is to express more of the endogenous *E. coli* IspG system. The systems, compositions of recombinant cells, and methods described herein utilize a different approach where IspG polypeptide activity and subsequent isoprene production is enhanced by over-expression of two types of IspG polypeptide-encoding nucleic acids. In one aspect, the two types of IspG polypeptides are *E. coli* and *T. elongatus* IspG polypeptides. In some aspects, the IspG polypeptide are encoded by heterologous nucleic acids. In other aspects, the IspG polypeptide are encoded by one or more copies of endogenous nucleic acids that are introduced to the host cell (e.g., *E. coli*). In any of these aspects, the nucleic acids may be introduced to the host cell (e.g., *E. coli*) by one or multiple plasmids. In other aspects, the nucleic acids may be introduced to the host cell (e.g., *E. coli*) by integration into the host cell's chromosome. One of skill in the art would appreciate that integration should occur at a location that is not essential to the host cell. For example, in a bacterial cell (e.g., *E. coli* cell), integration into the origin of replication (or any other essential region of the chromosome) would render the bacteria unable to replicate. Thus, care should be taken to avoid integrating into essential locations of the chromosome in the host organism.

The *E. coli* IspG system includes, but is not limited to, the enzyme IspG (encoded by the gene ispG) and the required flavodoxin redox partner FldA (encoded by the gene fldA). The *T. elongatus* IspG system includes, but is not limited to, the enzyme IspG (encoded by the gene gcpE) and the required ferredoxin redox partner Fd (encoded by the petF gene), as well as the nonessential ferredoxin-NADP(+) oxidoreductase redox partner Fpr (encoded by the petH gene). In some instances, Fpr activity is not required for the *T. elongatus* IspG to function within *E. coli* where the activity of the *T. elongatus* IspG was found to be dependent on the Fd cofactor. The fpr gene of *E. coli* is nonessential and the activity of the *T. elongatus* IspG within *E. coli* depends on co-expression of the *T. elongatus* Fd.

Without being bound by theory, the *E. coli* IspG system and the *T. elongatus* IspG system are believed to ultimately obtain the electrons necessary to perform their catalytic function from NADPH via some flavodoxin/ferredoxin-NADP(+) oxidoreductase activity. Enzymes with flavodoxin/ferredoxin-NADP(+) oxidoreductase activity have been demonstrated in vitro to fulfill the role of electron transport to the required flavodoxin and ferredoxin cofactors essential for IspG activity, however the in vivo physiological relevance of these reductases has not been shown and, as such, cannot be predictable.

Exemplary Polypeptides and Nucleic Acids

As noted above, recombinant cells of the invention and their progeny are engineered to have two types of IspG enzymes, isoprene synthase and one or more other DXP pathway polypeptide(s). In some aspect, the cell can further contain various iron-sulfur cluster-interacting redox polypeptides and nucleic acids, MVA pathway polypeptides and nucleic acids, DXP pathway associated polypeptides (e.g., DXP partner proteins) and nucleic acids, PGL polypeptides and nucleic acids and IDI polypeptides and nucleic acids.

Polypeptides includes polypeptides, proteins, peptides, fragments of polypeptides, and fusion polypeptides. In some aspects, the fusion polypeptide includes part or all of a first polypeptide (e.g., an iron-sulfur cluster-interacting redox polypeptide, DXP pathway polypeptide, DXP pathway associated polypeptide (e.g., DXP partner proteins), isoprene synthase polypeptide, and IDI polypeptide, or catalytically active fragment thereof) and may optionally include part or all of a second polypeptide (e.g., a peptide that facilitates purification or detection of the fusion polypeptide, such as a His-tag). In some aspects, the fusion polypeptide has an activity of two or more DXP pathway polypeptides.

In particular aspects, the nucleic acid includes a segment of or the entire nucleic acid sequence of any iron-sulfur cluster-interacting redox nucleic acid, IspG nucleic acid, DXP pathway nucleic acid, DXP pathway associated nucleic acid (e.g., DXP partner proteins), isoprene synthase nucleic acid, or IDI nucleic acid. In some aspects, the nucleic acid includes at least or about 50, 100, 150, 200, 300, 400, 500, 600, 700, 800, or more contiguous nucleotides from a iron-sulfur cluster-interacting redox nucleic acid, IspG, DXP pathway nucleic acid, DXP pathway associated nucleic acid, isoprene synthase nucleic acid, or IDI nucleic acid. In some aspects, the nucleic acid has one or more mutations compared to the sequence of a wild-type (i.e., a sequence occurring in nature) IspG nucleic acid, iron-sulfur cluster-interacting redox nucleic acid, DXP pathway nucleic acid, DXP pathway associated nucleic acid, isoprene synthase nucleic acid, or IDI nucleic acid. In some aspects, the nucleic acid has one or more mutations (e.g., a silent mutation) that increase the transcription or translation of IspG nucleic acid, iron-sulfur cluster-interacting redox nucleic acid, DXP pathway nucleic acid, DXP pathway associated nucleic acid, isoprene synthase nucleic acid, or IDI nucleic acid. In some aspects, the nucleic acid is a degenerate variant of any nucleic acid encoding an IspG polypeptide, iron-sulfur cluster-interacting redox polypeptide, DXP pathway polypeptide, DXP pathway associated polypeptide, isoprene synthase polypeptide, or IDI polypeptide.

The accession numbers of exemplary isoprene synthase and DXP pathway polypeptides and nucleic acids are listed in Appendix 1 of WO 2009/076676 and also further detailed herein.

Exemplary Iron-Sulfur Cluster-Interacting Redox Polypeptides and Nucleic Acids

Iron-sulfur cluster-interacting redox polypeptide plays an essential role in the DXP pathway for isoprenoid biosynthesis. Exemplary iron-sulfur cluster-interacting redox polypeptides include polypeptides, fragments of polypeptides, peptides, and fusions polypeptides that have at least one activity of a iron-sulfur cluster-interacting redox polypeptide. Standard methods can be used to determine whether a polypeptide has iron-sulfur cluster-interacting redox polypeptide activity by using a hydrogenase-linked assay measuring the rate of metronidazole[1-(2-hydroxyethyl)-2-methyl-5-nitroimidazole] reduction (Chen and Blanchard, Analytical Biochem, 93:216-222 (1979)).

Exemplary iron-sulfur cluster-interacting redox polypeptide nucleic acids include nucleic acids that encode a polypeptide, fragment of a polypeptide, peptide, or fusion polypeptide that has at least one activity of an iron-sulfur cluster-interacting redox polypeptide. Exemplary iron-sulfur cluster-interacting redox polypeptides and nucleic acids include naturally-occurring polypeptides and nucleic acids from any of the source organisms described herein as well as mutant polypeptides and nucleic acids derived from any of the source organisms described herein.

Iron-sulfur cluster-interacting redox polypeptide is a polypeptide that is capable of transferring electrons to a polypeptide containing an iron-sulfur cluster. An iron-sulfur cluster-interacting redox polypeptide includes, but is not limited to, flavodoxin (e.g., flavodoxin I), flavodoxin reductase, ferredoxin (e.g., ferredoxin I), ferredoxin-NADP+ oxidoreductase, and genes or polypeptides encoding thereof (e.g., fpr or fldA). For example, DXP pathway polypeptide HDS (GcpE) is a metallo-enzyme possessing a $[4Fe-4S]^{2+}$ center and catalyzes the reduction of cMEPP into HMBPP via two successive one-electron transfers mediated by the reduction of $[4Fe-4S]^{2+}$ center in the presence of flavodoxin/flavodoxin reductase (see, Wolff et al., *FEBS Letters*, 541:115-120 (2003)). Similarly, DXP pathway polypeptide HDR (LytB) is also a Fe/S protein catalyzing the reduction of HMBPP into IPP or DMAPP via two successive one-electron transfers in the presence of flavodoxin/flavodoxin reductase/ NADPH system. See, for example, Seemann, M. et al. *Agnew. Chem. Int. Ed.*, 41: 4337-4339 (2002); Wolff, M. et al., *FEBS Letters,* 541: 115-120 (2003)).

Flavodoxin is a protein that is capable of transferring electrons and contains the prosthetic group flavin mononucleotide. In *Escherichia coli* (*E. coli*), flavodoxin is encoded by the fldA gene and reduced by the FAD-containing protein NADPH:ferredoxin oxidoreductase, and plays an essential role in the DXP pathway for isoprenoid biosynthesis (see, example, Kia-Joo, P. et al. *FEBS Letters*, 579: 3802-3806, 2005).

Ferredoxin is a protein that is capable of transferring electron and contains iron and labile sulfur in equal amounts and plays an essential role in the DXP pathway for isoprenoid biosynthesis. For example, HDS from plants and cyanobacteria have been shown to be ferredoxin, rather than flavodoxin-dependent, enzymes (Seemann et al., *FEBS Lett.,* 580(6):1547-52 (2006)).

Fpr encodes flavodoxin/ferredoxin NADPH-oxidoreductase and provides the necessary electron derived from NADPH via FldA for HDS and HDR to perform their catalytic functions (reviewed in report by L. A. Furgerson, *The Mevalonate-Independent Pathway to Isoprenoid Compounds: Discovery, Elucidation, and Reaction Mechanisms*, published Feb. 13, 2006).

Exemplary DXP Pathway Polypeptides and Nucleic Acids

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, IDI polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein.

In particular, DXS polypeptides convert pyruvate and D-glyceraldehyde 3-phosphate into 1-deoxy-d-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-d-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2,4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2,4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate (HMBPP or HDMAPP) into isopentenyl diphosphate (IPP) and dimethylallyl diphosphate (DMAPP). In one embodiment, the ispH gene can be used to encode for HDR polypeptides. IspH is also known as 1-hydroxy-2-methyl-2-(E)-butenyl 4-diphosphate reductase, 4Fe-4S protein, LytB, ECK0030, JW0027, lytB, yaaE, and b0029. Standard methods can be used to determine whether a polypeptide has HDR polypeptides activity by measuring the ability of the polypeptide to convert HMBPP in vitro, in a cell extract, or in vivo.

IDI polypeptides convert isopentenyl diphosphate into dimethylallyl diphosphate. Standard methods can be used to determine whether a polypeptide has IDI polypeptides activity by measuring the ability of the polypeptide to convert isopentenyl diphosphate in vitro, in a cell extract, or in vivo.

Exemplary Polypeptides and nucleic acids associated with DXP Pathway

Various polypeptides associated with DXP pathway (e.g., DXP partner proteins) and nucleic acids encoding for those polypeptides can be used in conjunction with any one or more of the isoprene synthase(s), DXP pathway polypeptide(s) and/or MVA pathway polypeptide(s). In one embodiment, chaperonins can be used. Chaperonins facilitate the folding and un-folding of proteins, an activity required for the competent tertiary structure to be attained. Chaperones of this class are involved in both generating and repairing the 3-D structure of proteins, working to achieve and maintain protein functionality. The *E. coli* chaperonins DnaK and GroEL/GroES are well characterized examples of such enzymes (Bukau et al., *Cell*, 92:351-366 (1998)). Chaperonins facilitate the delivery, maintenance, and repair of cofactors required for enzyme catalysis. In one embodiment, such chaperonins can be those enzyme chaperones involved in the functionality of iron-sulfur cluster cofactors. The iscR operon genes hrcA, hrcB, and iscA as well as erpA and the additional A-type carrier proteins of *E. coli* are non-limiting examples of the class of chaperonins which can be used, serving among those involved in the delivery, maintenance, and repair of iron-sulfur clusters within *E. coli* (Tokumoto and Takahashi, *J. Biochem.*, 130: 63-71 (2001); Loiseau et al., *PNAS*, 104 (34): 13626-13631 (2007); Vinella et al., *PLOS Genetics*, 5(5): 1-16 of e1000497 (2009)). In another embodiment, the iscS gene can be used. In addition to the better characterized role in de novo iron-sulfur cluster biogenesis, the iscS gene has been implicated in repair of damaged iron-sulfur clusters and can serve as an example of said chaperone (Djaman et al., *J. Biol. Chem.*, 279(43): 44590-44599 (2004). Similarly, the Ric protein encoded by ytfE and ferritin A encoded by ftn of *E. coli* are further examples of chaperonins involved in the repair of iron-sulfur clusters (Justino et al., *Biometals*, 22: 99-108 (2009); Justino et al., *J. Biol. Chem.*, 282(14): 10352-10359 (2007); Bitoun et al., *Biometals*, 21: 693-703 (2008).

Exemplary Isoprene Synthase Polypeptides and Nucleic Acids

As noted above, isoprene synthase polypeptides convert dimethylallyl diphosphate (DMAPP) into isoprene. Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein.

In some aspects of the invention, the recombinant cells described in any of the compositions or methods described herein further comprise one or more nucleic acids encoding an isoprene synthase polypeptide or a polypeptide having isoprene synthase activity. In some aspects, the isoprene synthase polypeptide is an endogenous polypeptide. In some aspects, the endogenous nucleic acid encoding an isoprene synthase polypeptide is operably linked to a constitutive promoter. In some aspects, the endogenous nucleic acid encoding an isoprene synthase polypeptide is operably linked to an inducible promoter. In some aspects, the endogenous nucleic acid encoding an isoprene synthase polypeptide is operably linked to a strong promoter. In some aspects, more than one endogenous nucleic acid encoding an isoprene synthase polypeptide is used (e.g, 2, 3, 4, or more copies of an endogenous nucleic acid encoding an isoprene synthase polypeptide). In a particular aspect, the cells are engineered to overexpress the endogenous isoprene synthase pathway polypeptide relative to wild-type cells. In some aspects, the endogenous nucleic acid encoding an isoprene synthase polypeptide is operably linked to a weak promoter.

In some aspects, the isoprene synthase polypeptide is a heterologous polypeptide. In some aspects, the cells comprise more than one copy of a heterologous nucleic acid encoding an isoprene synthase polypeptide. In some aspects, the heterologous nucleic acid encoding an isoprene synthase polypeptide is operably linked to a constitutive promoter. In some aspects, the heterologous nucleic acid encoding an isoprene synthase polypeptide is operably linked to an inducible promoter. In some aspects, the heterologous nucleic acid encoding an isoprene synthase polypeptide is operably linked to a strong promoter. In some aspects, the heterologous nucleic acid encoding an isoprene synthase polypeptide is operably linked to a weak promoter.

The nucleic acids encoding an isoprene synthase polypeptide(s) can be integrated into a genome of the host cells or can be stably expressed in the cells. The nucleic acids encoding an isoprene synthase polypeptide(s) can additionally be on a vector.

In some aspects, the isoprene synthase polypeptide or nucleic acid is from the family Fabaceae, such as the Faboideae subfamily. In some aspects, the isoprene synthase polypeptide is a polypeptide from *Pueraria* or *Populus* or a hybrid such as *Populus alba* x *Populus tremula*. In some aspects, the isoprene synthase polypeptide or nucleic acid is a polypeptide or nucleic acid from *Pueraria montana* (kudzu) (Sharkey et al., Plant Physiology 137: 700-712, 2005), *Pueraria lobata*, poplar (such as *Populus alba, Populus nigra, Populus trichocarpa*, or *Populus alba* x *tremula* (CAC35696) Miller et al., Planta 213: 483-487, 2001) aspen (such as *Populus tremuloides*) Silver et al., JBC 270(22): 13010-1316, 1995), or English Oak (*Quercus robur*) (Zimmer et al., WO 98/02550). Suitable isoprene synthases include, but are not limited to, those identified by Genbank Accession Nos. AY341431, AY316691, AY279379, AJ457070, and AY182241. In some aspects, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some aspects, the isoprene synthase nucleic acid or polypeptide is a naturally-occurring polypeptide or nucleic acid from poplar. In some aspects, the isoprene synthase nucleic acid or polypeptide is not a naturally-occurring polypeptide or nucleic acid from poplar.

In some aspects, the isoprene synthase nucleic acid or polypeptide is a naturally-occurring polypeptide or nucleic acid (e.g., naturally-occurring polypeptide or nucleic acid from *Populus*). In some aspects, the isoprene synthase nucleic acid or polypeptide is not a wild-type or naturally-occurring polypeptide or nucleic acid. In some aspects, the isoprene synthase nucleic acid or polypeptide is a variant of a wild-type or naturally-occurring polypeptide or nucleic acid (e.g., a variant of a wild-type or naturally occurring polypeptide or nucleic acid from *Populus*).

In some aspects, the isoprene synthase polypeptide is a variant. Variants of isoprene synthase can possess improved activity such as improved enzymatic activity. In some aspects, an isoprene synthase variant has other improved properties, such as improved stability (e.g., thermo-stability), and/or improved solubility. In some aspects, the isoprene synthase polypeptide is a variant of a wild-type or naturally occurring isoprene synthase. In some aspects, the variant has improved activity such as improved catalytic activity compared to the wild-type or naturally occurring isoprene synthase. The increase in activity (e.g., catalytic activity) can be at least about any of 10%, 20%, 30%, 40%, 50%, 60%, 70%, 80%, 90%, or 95%. In some aspects, the increase in activity such as catalytic activity is at least about any of 1 fold, 2 folds, 5 folds, 10 folds, 20 folds, 30 folds, 40 folds, 50 folds, 75 folds, or 100 folds. In some aspects, the increase in activity such as catalytic activity is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the variant has improved solubility compared to the wild-type or naturally occurring isoprene synthase. The increase in solubility can be at least about any of 10%, 20%, 30%, 40%, 50%, 60%, 70%, 80%, 90%, or 95%. The increase in solubility can be at least about any of 1 fold, 2 folds, 5 folds, 10 folds, 20 folds, 30 folds, 40 folds, 50 folds, 75 folds, or 100 folds. In some aspects, the increase in solubility is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the isoprene synthase polypeptide is a variant of naturally occurring isoprene synthase and has improved stability (such as thermo-stability) compared to the naturally occurring isoprene synthase.

In some aspects, the variant has at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200% of the activity of a wild-type or naturally occurring isoprene synthase. The variant can share sequence similarity with a wild-type or naturally occurring isoprene synthase. In some aspects, a variant of a wild-type or naturally occurring isoprene synthase can have at least about any of 40%, 50%, 60%, 70%, 75%, 80%, 90%, 91%, 92%, 93%, 94%, 95%, 96%, 97%, 98%, 99%, 99.5%, or 99.9% amino acid sequence identity as that of the wild-type or naturally occurring isoprene synthase. In some aspects, a variant of a wild-type or naturally occurring isoprene synthase has any of about 70% to about 99.9%, about 75% to about 99%, about 80% to about 98%, about 85% to about 97%, or about 90% to about 95% amino acid sequence identity as that of the wild-type or naturally occurring isoprene synthase.

In some aspects, the variant comprises a mutation in the wild-type or naturally occurring isoprene synthase. In some aspects, the variant has at least one amino acid substitution, at least one amino acid insertion, and/or at least one amino acid deletion. In some aspects, the variant has at least one amino acid substitution. In some aspects, the number of differing amino acid residues between the variant and wild-type or naturally occurring isoprene synthase can be one or more, e.g. 1, 2, 3, 4, 5, 10, 15, 20, 30, 40, 50, or more amino acid residues. Naturally occurring isoprene synthases can include any isoprene synthases from plants, for example, kudzu isoprene synthases, poplar isoprene synthases, English oak isoprene synthases, and willow isoprene synthases. In some aspects, the variant is a variant of isoprene synthase from *Populus alba*. In some aspects, the variant of isoprene synthase from *Populus alba* has at least one amino acid substitution, at least one amino acid insertion, and/or at least one amino acid deletion. In some aspects, the variant is a truncated *Populus alba* isoprene synthase. In some aspects, the nucleic acid encoding variant (e.g., variant of isoprene synthase from *Populus alba*) is codon optimized (for example, codon optimized based on host cells where the heterologous isoprene synthase is expressed).

The isoprene synthase polypeptide provided herein can be any of the isoprene synthases or isoprene synthase variants described in WO 2009/132220, WO 2010/124146, U.S. Patent Application Publication No.: 2010/0086978, US Appl. 13/283,564 and PCT/US2011/058188, the contents of which are expressly incorporated herein by reference in their entirety with respect to the isoprene synthases and isoprene synthase variants. Suitable isoprene synthases include, but are not limited to, those identified by Genbank Accession Nos. AY341431, AY316691, AY279379, AJ457070, and AY182241. Types of isoprene synthases which can be used in any one of the compositions or methods including methods of making microorganisms encoding isoprene synthase described herein are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/124146, WO2010/078457, and WO2010/148256, the contents of which are expressly incorporated herein by reference in their entirety with respect to the isoprene synthases and isoprene synthase variants.

Any one of the promoters described herein (e.g., promoters described herein and identified in the Examples of the present disclosure including inducible promoters and constitutive promoters) can be used to drive expression of any of the isoprene synthases described herein.

Standard methods can be used to determine whether a polypeptide has isoprene synthase polypeptide activity by measuring the ability of the polypeptide to convert DMAPP into isoprene in vitro, in a cell extract, or in vivo. In an exemplary assay, cell extracts are prepared by growing a strain (e.g., the *E. coli*/pTrcKudzu strain described herein) in the shake flask method as described in Example 1. After induction is complete, approximately 10 mL of cells are pelleted by centrifugation at 7000×g for 10 minutes and resuspended in 5 ml of PEB without glycerol. The cells are lysed using a French Pressure cell using standard procedures. Alternatively the cells are treated with lysozyme (Ready-Lyse lysozyme solution; EpiCentre) after a freeze/thaw at −80 C.

Isoprene synthase polypeptide activity in the cell extract can be measured, for example, as described in Silver et al., J. Biol. Chem. 270:13010-13016, 1995 and references therein, which are each hereby incorporated by reference in their entireties, particularly with respect to assays for isoprene synthase polypeptide activity. DMAPP (Sigma) is evaporated to dryness under a stream of nitrogen and rehydrated to a concentration of 100 mM in 100 mM potassium phosphate buffer pH 8.2 and stored at −200 C. To perform the assay, a solution of 5 µL of 1M $MgCl_2$, 1 mM (250 µg/ml) DMAPP, 65 µL of Plant Extract Buffer (PEB) (50 mM Tris-HCl, pH 8.0, 20 mM $MgCl_2$, 5% glycerol, and 2 mM DTT) is added to 25 µL of cell extract in a 20 ml Headspace vial with a metal screw cap and teflon coated silicon septum (Agilent Technologies) and cultured at 37° C. for 15 minutes with shaking. The reaction can be quenched by adding 200 µL of 250 mM EDTA and quantified by GC/MS.

Exemplary MVA Pathway Polypeptides and Nucleic Acids

In some aspects of the invention, the cells described in any of the compositions or methods described herein comprise a nucleic acid encoding an MVA pathway polypeptide. In some aspects, the MVA pathway polypeptide is an endogenous polypeptide. In some aspects, the cells comprise one or more additional copies of an endogenous nucleic acid encoding an MVA pathway polypeptide. In some aspects, the endogenous nucleic acid encoding an MVA pathway polypeptide operably linked to a constitutive promoter. In some aspects, the endogenous nucleic acid encoding an MVA pathway polypeptide operably linked to a constitutive promoter. In some aspects, the endogenous nucleic acid encoding an MVA pathway polypeptide is operably linked to a strong promoter. In a particular aspect, the cells are engineered to over-express the endogenous MVA pathway polypeptide relative to wild-type cells.

In some aspects, the MVA pathway polypeptide is a heterologous polypeptide. In some aspects, the cells comprise more than one copy of a heterologous nucleic acid encoding an MVA pathway polypeptide. In some aspects, the heterologous nucleic acid encoding an MVA pathway polypeptide is operably linked to a constitutive promoter. In some aspects, the heterologous nucleic acid encoding an MVA pathway polypeptide is operably linked to a strong promoter.

Exemplary MVA pathway polypeptides include acetyl-CoA acetyltransferase (AA-CoA thiolase) polypeptides, acetoacetyl-CoA synthase (which utilizes acetyl-CoA and malonyl-CoA), 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein. In addition, variants of MVA pathway polypeptide that confer the result of better isoprene production can also be used as well.

In certain aspects, the one or more nucleic acids encoding one or more MVA pathway polypeptides is a heterologous nucleic acid. In other aspects, the one or more nucleic acids encoding one or more MVA pathway polypeptides is a copy of an endogenous nucleic acid. In any of the aspects herein, one or more MVA pathway polypeptides can be selected from (a) an enzyme that condenses two molecules of acetyl-CoA to form acetoacetyl-CoA (AA-CoA thiolase) or an enzyme that can synthesize acetoacetyl-CoA from malonyl-CoA and acetyl-CoA (acetoacetyl-CoA synthase); (b) an enzyme that condenses acetoacetyl-CoA with acetyl-CoA to form HMG-CoA (e.g., HMG synthase); (c) an enzyme that converts HMG-CoA to mevalonate; (d) an enzyme that phosphorylates mevalonate to mevalonate 5-phosphate; (e) an enzyme that converts mevalonate 5-phosphate to mevalonate 5-pyrophosphate; (f) an enzyme that converts mevalonate 5-pyrophosphate to isopentenyl pyrophosphate; and (g) an enzyme that converts isopentenyl pyrophosphate to dimethylallyl diphosphate. In any of the aspects herein, one or more MVA pathway polypeptides is selected from (a) an enzyme that condenses acetoacetyl-CoA with acetyl-CoA to form HMG-CoA (e.g., HMG synthase); (b) an enzyme that converts HMG-CoA to mevalonate; (c) an enzyme that phosphorylates mevalonate to mevalonate 5-phosphate; (d) an enzyme that converts mevalonate 5-phosphate to mevalonate 5-pyrophosphate; and (e) an enzyme that converts mevalonate 5-pyrophosphate to isopentenyl pyrophosphate.

Types of MVA pathway polypeptides and/or DXP pathway polypeptides which can be used and methods of making microorganisms encoding MVA pathway polypeptides and/or DXP pathway polypeptides are also described in International Patent Application Publication No. WO2009/076676.

One of skill in the art can readily select and/or use suitable promoters to optimize the expression of isoprene synthase or and one or more MVA pathway polypeptides and/or one or more DXP pathway polypeptides. Similarly, one of skill in the art can readily select and/or use suitable vectors (or transfer vehicle) to optimize the expression of isoprene synthase or and one or more MVA pathway polypeptides and/or one or more DXP pathway polypeptides. In some aspects, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some aspects, an isoprene synthase or MVA pathway nucleic acid integrates into a chromosome of the cells without a selective marker.

Exemplary Source Organisms

Figure 3:
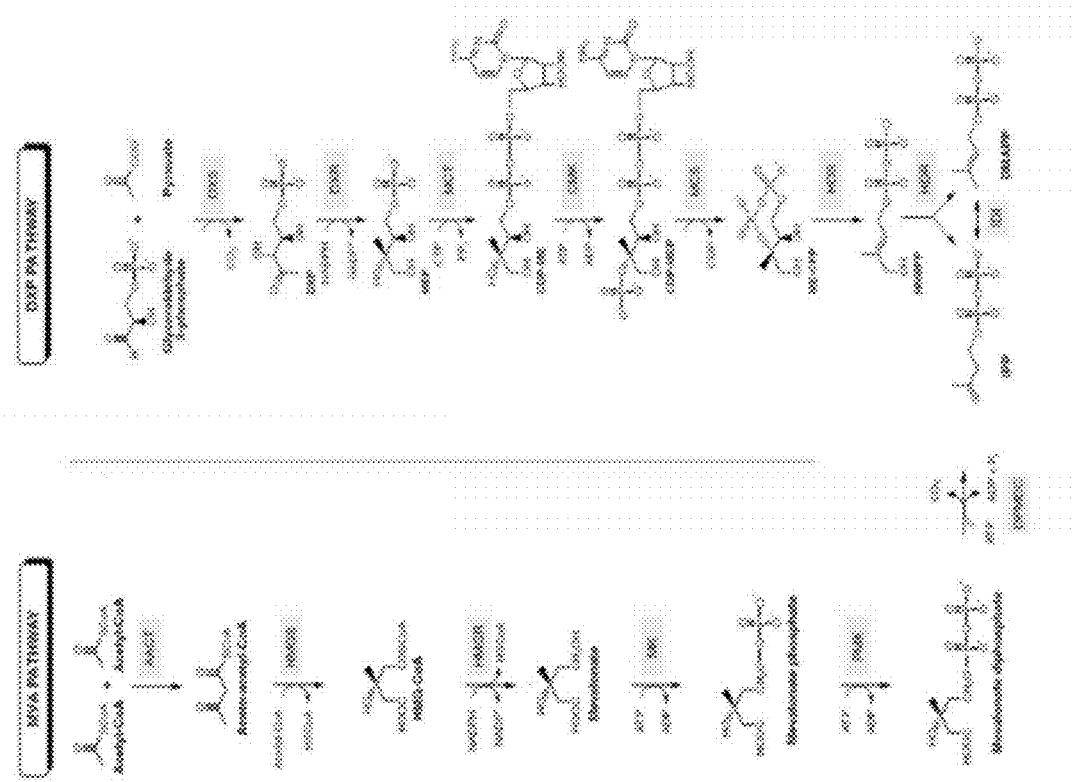
FIG. 3 shows MVA and DXP metabolic pathways for isoprene (based on F. Bouvier et al., Progress in Lipid Res. 44:357-429, 2005). The following description includes alternative names for each polypeptide in the pathways and a reference that discloses an assay for measuring the activity of the indicated polypeptide (each of these references are each hereby incorporated herein by reference in their entireties). Mevalonate Pathway: AACT; Acetyl-CoA acetyltransferase, MvaE, EC 2.3.1.9. Assay: J. Bacteriol. 184:2116-2122, 2002; HMGS; Hydroxymethylglutaryl-CoA synthase, MvaS, EC 2.3.3.10. Assay: J. Bacteriol. 184:4065-4070, 2002; HMGR; 3-Hydroxy-3-methylglutaryl-CoA reductase, MvaE, EC 1.1.1.34. Assay: J. Bacteriol. 184:2116-2122, 2002; MVK; Mevalonate kinase, ERG12, EC 2.7.1.36. Assay: Curr Genet 19:9-14, 1991. PMK; Phosphomevalonate kinase, ERG8, EC 2.7.4.2, Assay: Mol. Cell. Biol. 11:620-631, 1991; DPMDC; Diphosphomevalonate decarboxylase, MVD1, EC 4.1.1.33. Assay: Biochemistry 33:13355-13362, 1994; IDI; Isopentenyl-diphosphate delta-isomerase, IDI1, EC 5.3.3.2. Assay: J. Biol. Chem. 264:19169-19175, 1989. DXP Pathway: DXS; 1-Deoxyxylulose-5-phosphate synthase, dxs, EC 2.2.1.7. Assay: PNAS 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS 97: 6451-6456, 2000; CMK; 4-Diphosphocytidyl-2-C-methyl-D-erythritol kinase, IspE, EC 2.7.1.148. Assay: PNAS 97:1062-1067, 2000; MCS; 2C-Methyl-D-erythritol 2,4-cyclodiphosphate synthase, IspF, EC 4.6.1.12. Assay: PNAS 96:11758-11763, 1999; HDS; 1-Hydroxy-2-methyl-2-(E)-butenyl 4-diphosphate synthase, ispG, EC 1.17.4.3. Assay: J. Org. Chem. 70:9168-9174, 2005; HDR; 1-Hydroxy-2-methyl-2-(E)-butenyl 4-diphosphate reductase, IspH, EC 1.17.1.2. Assay: JACS 126:12847-12855, 2004.

Iron-sulfur cluster-interacting redox nucleic acid, DXP pathway nucleic acid, DXP pathway associated nucleic acid, isoprene synthase nucleic acid, or IDI nucleic acid (and their encoded polypeptides) can be obtained from any organism that naturally includes iron-sulfur cluster-interacting redox nucleic acid, DXP pathway nucleic acid, DXP pathway associated nucleic acid, isoprene synthase nucleic acid, and/or IDI nucleic acid. As noted above, isoprene is formed naturally by a variety of organisms, such as bacteria, yeast, plants, and animals. Organisms include the MVA pathway, DXP pathway, or both the MVA and DXP pathways for producing isoprene (FIG. 3). Thus, DXS, DXR, MCT, CMK, MCS, HDS, or HDR nucleic acids can be obtained, e.g., from any organism that has the DXP pathway or has both the MVA and DXP pathways. IDI and isoprene synthase nucleic acids can be obtained, e.g., from any organism that contains the MVA pathway, DXP pathway, or both the MVA and DXP pathways.

In some aspects, the nucleic acid sequence of the iron-sulfur cluster-interacting redox nucleic acid, DXP pathway nucleic acid, DXP pathway associated nucleic acid, isoprene synthase nucleic acid, or IDI nucleic acid is identical to the sequence of a nucleic acid that is produced by any of the following organisms in nature. In some aspects, the amino acid sequence of iron-sulfur cluster-interacting redox polypeptide, DXP pathway polypeptide, DXP pathway associated polypeptide, isoprene synthase polypeptide, or IDI polypeptide is identical to the sequence of a polypeptide that is produced by any of the following organisms in nature. In some aspects, the iron-sulfur cluster-interacting redox nucleic acid, DXP pathway nucleic acid, DXP pathway associated nucleic acid, isoprene synthase nucleic acid, or IDI nucleic acid or its encoded polypeptide is a mutant nucleic acid or polypeptide derived from any of the organisms described herein. As used herein, "derived from" refers to the source of the nucleic acid or polypeptide into which one or more mutations is introduced. For example, a polypeptide that is "derived from a plant polypeptide" refers to polypeptide of interest that results from introducing one or more mutations into the sequence of a wild-type (i.e., a sequence occurring in nature) plant polypeptide.

In some aspects, the source organism is a fungus, examples of which are species of *Aspergillus* such as *A. oryzae* and *A. niger*, species of *Saccharomyces* such as *S. cerevisiae*, species of *Schizosaccharomyces* such as *S. pombe*, and species of *Trichoderma* such as *T. reesei*. In some aspects, the source organism is a filamentous fungal cell. The term "filamentous fungi" refers to all filamentous forms of the subdivision Eumycotina (see, Alexopoulos, C. J. (1962), Introductory Mycology, Wiley, New York). These fungi are characterized by a vegetative mycelium with a cell wall composed of chitin, cellulose, and other complex polysaccharides. The filamentous fungi are morphologically, physiologically, and genetically distinct from yeasts. Vegetative growth by filamentous fungi is by hyphal elongation and carbon catabolism is obligatory aerobic. The filamentous fungal parent cell may be a cell of a species of, but not limited to, *Trichoderma*, (e.g., *Trichoderma reesei*, the asexual morph of *Hypocrea jecorina*, previously classified as *T. longibrachiatum*, *Trichoderma viride*, *Trichoderma koningii*, *Trichoderma harzianum*) (Sheir-Neirs et al., Appl. Microbiol. Biotechnol 20: 46-53, 1984; ATCC No. 56765 and ATCC No. 26921); *Penicillium* sp., *Humicola* sp. (e.g., *H. insolens*, *H. lanuginose*, or *H. grisea*); *Chrysosporium* sp. (e.g., *C. lucknowense*), *Gliocladium* sp., *Aspergillus* sp. (e.g., *A. oryzae*, *A. niger*, *A sojae*, *A. japonicus*, *A. nidulans*, or *A. awamori*) (Ward et al., Appl. Microbiol. Biotechnol. 39: 7380743, 1993 and Goedegebuur et al., Genet 41: 89-98, 2002), *Fusarium* sp., (e.g., *F. roseum*, *F. graminum F. cerealis*, *F. oxysporuim*, or *F. venenatum*), *Neurospora* sp., (e.g., *N. crassa*), *Hypocrea* sp., *Mucor* sp., (e.g., *M. miehei*), *Rhizopus* sp. and *Emericella* sp. (see also, Innis et al., Sci. 228: 21-26, 1985). The term "*Trichoderma*" or "*Trichoderma* sp." or "*Trichoderma* spp." refer to any fungal genus previously or currently classified as *Trichoderma*.

In some aspects, the fungus is *A. nidulans*, *A. awamori*, *A. oryzae*, *A. aculeatus*, *A. niger*, *A. japonicus*, *T. reesei*, *T. viride*, *F. oxysporum*, or *F. solani*. *Aspergillus* strains are disclosed in Ward et al., Appl. Microbiol. Biotechnol. 39:738-743, 1993 and Goedegebuur et al., Curr Gene 41:89-98, 2002, which are each hereby incorporated by reference in their entireties, particularly with respect to fungi. In particular aspects, the fungus is a strain of *Trichoderma*, such as a strain of *T. reesei*. Strains of *T. reesei* are known and non-limiting examples include ATCC No. 13631, ATCC No. 26921, ATCC No. 56764, ATCC No. 56765, ATCC No. 56767, and NRRL 15709, which are each hereby incorporated by reference in their entireties, particularly with respect to strains of *T. reesei*. In some aspects, the host strain is a derivative of RL-P37. RL-P37 is disclosed in Sheir-Neiss et al., Appl. Microbiol. Biotechnology 20:46-53, 1984.

In some aspects, the source organism is a yeast, such as *Saccharomyces* sp., *Schizosaccharomyces* sp., *Pichia* sp., or *Candida* sp.

In some aspects, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Thermosynechococcus* such as *T. elongatus*, strains of *Sinorhizobium* such as *S. meliloti*, strains of *Helicobacter* such as *H. pylori*, strains of *Agrobacterium* such as *A. tumefaciens*, strains of *Deinococcus* such as *D. radiodurans*, strains of *Listeria* such as *L. monocytogenes*, strains of *Lactobacillus* such as L. spp, or strains of *Escherichia* such as *E. coli*.

As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxyba-*

*cillus, Brevibacillus, Filobacillus, Gracilibacillus, Halobacillus, Paenibacillus, Salibacillus, Thermobacillus, Ureibacillus,* and *Virgibacillus*.

In some aspects, the source organism is a gram-positive bacterium. Non-limiting examples include strains of *Streptomyces* (e.g., *S. lividans, S. coelicolor*, or *S. griseus*), *Bacillus, Listeria* (e.g., *L. monocytogenes*) or *Lactobacillus* (e.g., *L.* spp). In some aspects, the source organism is a gram-negative bacterium, such as *E. coli, Pseudomonas* sp, or *H. pylori*.

In some aspects, the source organism is a plant, such as a plant from the family Fabaceae, such as the Faboideae subfamily. In some aspects, the source organism is kudzu, poplar (such as *Populus alba* x *tremula* CAC35696), aspen (such as *Populus tremuloides*), *Quercus robur, Arabidopsis* (such as *A. thaliana*), or *Zea* (such as *Z. mays*).

In some aspects, the source organism is an algae, such as a green algae, red algae, glaucophytes, chlorarachniophytes, euglenids, chromista, or dinoflagellates.

In some aspects, the source organism is a cyanobacterium, such as a cyanobacterium classified into any of the following groups based on morphology: Chroococcales, Pleurocapsales, Oscillatoriales, Nostocales, or Stigonematales. In some aspects, the cyanobacterium is *Thermosynechococcus* elongates.

Exemplary Host Cells

A variety of host cells can be used to express iron-sulfur cluster-interacting redox polypeptide, DXP pathway polypeptide, DXP pathway associated polypeptide, MVA pathway polypeptide, MVA pathway associated polypeptide, isoprene synthase polypeptide, or IDI polypeptide and to produce isoprene in the methods of the claimed invention. Exemplary host cells include cells from any of the organisms listed in the prior section under the heading "Exemplary Source Organisms." The host cell may be a cell that naturally produces isoprene or a cell that does not naturally produce isoprene. In some aspects, the host cell naturally produces isoprene using the DXP pathway and an isoprene synthase, and one or more DXP pathway polypeptide and iron-sulfur cluster-interacting redox polypeptides are added to enhance production of isoprene using this pathway. In some aspects, the host cell naturally produces isoprene using the DXP pathway and isoprene synthase, and one or more DXP pathway nucleic acids, one or more iron-sulfur cluster-interacting redox nucleic acids, and IDI are added to enhance production of isoprene using this pathway.

Thus, one of skill in the art will recognize that expression vectors can be designed to contain certain components which optimize gene expression for certain host strains. Such optimization components include, but are not limited to origin of replication, promoters, and enhancers. The vectors and components referenced herein are described for exemplary purposes and are not meant to narrow the scope of the invention.

Any cell or progeny thereof that can be used to heterologously express genes can be used herein to express iron-sulfur cluster-interacting redox polypeptide, DXP pathway polypeptide, DXP pathway associated polypeptide, MVA pathway polypeptide, MVA pathway associated polypeptide, isoprene synthase polypeptide, or IDI polypeptide and to produce isoprene in the methods of the claimed invention. In some embodiments, the host cell is a gram-positive bacterium. Non-limiting examples include strains of *Streptomyces* (e.g., *S. lividans, S. coelicolor*, or *S. griseus*), *Bacillus, Listeria* (e.g., *L. monocytogenes*) or *Lactobacillus* (e.g., *L.* spp). In some embodiments, the source organism is a gram-negative bacterium, such as *E. coli, Pseudomonas* sp, or *H. pylori*. In certain embodiments, *E. coli* host cells can be used to express one or more iron-sulfur cluster-interacting redox polypeptide, DXP pathway polypeptide, DXP pathway associated polypeptide, MVA pathway polypeptide, MVA pathway associated polypeptide, isoprene synthase polypeptide, or IDI polypeptide and to produce isoprene in the methods of the claimed invention.

Bacteria cells, including gram positive or gram negative bacteria can be used to express any of the heterologous genes described above. In particular, any one of *P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells.

There are numerous types of anaerobic cells that can be used as host cells in the compositions and methods of the present invention. In one aspect of the invention, the cells described in any of the compositions or methods described herein are obligate anaerobic cells and progeny thereof. Obligate anaerobes typically do not grow well, if at all, in conditions where oxygen is present. It is to be understood that a small amount of oxygen may be present, that is, there is some tolerance level that obligate anaerobes have for a low level of oxygen. In one aspect, obligate anaerobes engineered to produce mevalonate, isoprenoid precursors, isoprene, and isoprenoids can serve as host cells for any of the methods and/or compositions described herein and are grown under substantially oxygen-free conditions, wherein the amount of oxygen present is not harmful to the growth, maintenance, and/or fermentation of the anaerobes.

In another aspect of the invention, the host cells described and/or used in any of the compositions or methods described herein are facultative anaerobic cells and progeny thereof. Facultative anaerobes can generate cellular ATP by aerobic respiration (e.g., utilization of the TCA cycle) if oxygen is present. However, facultative anaerobes can also grow in the absence of oxygen. This is in contrast to obligate anaerobes which die or grow poorly in the presence of greater amounts of oxygen. In one aspect, therefore, facultative anaerobes can serve as host cells for any of the compositions and/or methods provided herein and can be engineered to produce mevalonate, isoprenoid precursors, isoprene, and isoprenoids. Facutative anerobic host cells can be grown under substantially oxygen-free conditions, wherein the amount of oxygen present is not harmful to the growth, maintenance, and/or fermentation of the anaerobes, or can be alternatively grown in the presence of greater amounts of oxygen.

The host cell can additionally be a filamentous fungal cell and progeny thereof. (See, e.g., Berka & Barnett, *Biotechnology Advances*, (1989), 7(2):127-154). In some aspects, the filamentous fungal cell can be any of *Trichoderma longibrachiatum, T. viride, T. koningii, T. harzianum, Penicillium* sp., *Humicola insolens, H. lanuginose, H. grisea, Chrysosporium* sp., *C. lucknowense, Gliocladium* sp., *Aspergillus* sp., such as *A. oryzae, A. niger, A sojae, A. japonicus, A. nidulans*, or *A. awamori, Fusarium* sp., such as *F. roseum, F. graminum F. cerealis, F. oxysporuim*, or *F. venenatum, Neurospora* sp., such as *N. crassa, Hypocrea* sp., *Mucor* sp., such as *M. miehei, Rhizopus* sp. or *Emericella* sp. In some aspects, the fungus is *A. nidulans, A. awamori, A. oryzae, A. aculeatus, A. niger, A. japonicus, T. reesei, T. viride, F. oxysporum*, or *F. solani*. In certain embodiments, plasmids or plasmid components for use herein include those described in U.S. patent pub. No. US 2011/0045563.

The host cell can also be a yeast, such as *Saccharomyces* sp., *Schizosaccharomyces* sp., *Pichia* sp., or *Candida* sp. In some aspects, the *Saccharomyces* sp. is *Saccharomyces cerevisiae* (See, e.g., Romanos et al., *Yeast*, (1992), 8(6):423-

488). In certain embodiments, plasmids or plasmid components for use herein include those described in U.S. Pat. No. 7,659,097 and U.S. patent pub. No. US 2011/0045563.

The host cell can additionally be a species of algae, such as a green algae, red algae, glaucophytes, chlorarachniophytes, euglenids, chromista, or dinoflagellates. (See, e.g., Saunders & Warmbrodt, "*Gene Expression in Algae and Fungi, Including Yeast,*" (1993), National Agricultural Library, Beltsville, Md.). In certain embodiments, plasmids or plasmid components for use herein include those described in U.S. Patent Pub. No. US 2011/0045563. In some aspects, the host cell is a cyanobacterium, such as cyanobacterium classified into any of the following groups based on morphology: Chlorococcales, Pleurocapsales, Oscillatoriales, Nostocales, or Stigonematales (See, e.g., Lindberg et al., Metab. Eng., (2010) 12(1):70-79). In certain embodiments, plasmids or plasmid components for use herein include those described in U.S. patent pub. No. US 2010/0297749; US 2009/0282545 and Intl. Pat. Appl. No. WO 2011/034863.

Exemplary Transformation Methods

IspG nucleic acids, iron-sulfur cluster-interacting redox nucleic acid, DXP pathway nucleic acid, DXP pathway associated nucleic acid, isoprene synthase nucleic acid, or IDI nucleic acid or its vectors comprising them can be inserted into a host cell (e.g., *E. coli* cell, an algal cell, a plant cell, a fungal cell, a yeast cell, or a bacterial cell described herein) using standard techniques known to one of skill in the art. The introduced nucleic acids may be integrated into chromosomal DNA or maintained as extrachromosomal replicating sequences.

Additional Host cell Mutations

In certain embodiments in which the recombinant cells described herein further comprise one or more one or more MVA pathway polypeptides, the invention further contemplates certain host cell mutations that increase carbon flux through the MVA pathway. In another embodiment, the invention contemplates certain host cell mutations that increase carbon flux through the DXP pathway. In another embodiment, the invention contemplates certain host cell mutations that increase carbon flux through the DXP and MVA pathways. By increasing the carbon flow, more isoprene can be produced. In certain embodiments, the recombinant cells as described herein can also be engineered for increased carbon flux towards mevalonate production wherein the activity of one or more enzymes from the group consisting of: (a) citrate synthase; (b) phosphotransacetylase; (c) acetate kinase; (d) lactate dehydrogenase; (e) NADP-dependent malic enzyme, and; (f) pyruvate dehydrogenase is modulated.

Citrate Synthase Pathway

Citrate synthase catalyzes the condensation of oxaloacetate and acetyl-CoA to form citrate, a metabolite of the Tricarboxylic acid (TCA) cycle (Ner, S. et al. 1983. Biochemistry 22: 5243-5249; Bhayana, V. and Duckworth, H. 1984. Biochemistry 23: 2900-2905) (FIG. 5). In *E. coli*, this enzyme, encoded by gltA, behaves like a trimer of dimeric subunits. The hexameric form allows the enzyme to be allosterically regulated by NADH. This enzyme has been widely studied (Wiegand, G., and Remington, S. 1986. Annual Rev. Biophysics Biophys. Chem. 15: 97-117; Duckworth et al. 1987. Biochem Soc Symp. 54:83-92; Stockell, D. et al. 2003. J. Biol. Chem. 278: 35435-43; Maurus, R. et al. 2003. Biochemistry. 42:5555-5565). To avoid allosteric inhibition by NADH, replacement by or supplementation with the *Bacillus subtilis* NADH-insensitive citrate synthase has been considered (Underwood et al. 2002. Appl. Environ. Microbiol. 68:1071-1081; Sanchez et al. 2005. Met. Eng. 7:229-239).

The reaction catalyzed by citrate synthase is directly competing with the thiolase catalyzing the first step of the mevalonate pathway, as they both have acetyl-CoA as a substrate (Hedl et al. 2002. J. Bact. 184:2116-2122). Therefore, one of skill in the art can modulate citrate synthase expression (e.g., decrease enzyme activity) to allow more carbon to flux into the mevalonate pathway, thereby increasing the eventual production of mevalonate and isoprene. Decrease of citrate synthase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In some aspects, the activity of citrate synthase is modulated by decreasing the activity of an endogenous citrate synthase gene. This can be accomplished by chromosomal replacement of an endogenous citrate synthase gene with a transgene encoding an NADH-insensitive citrate synthase or by using a transgene encoding an NADH-insensitive citrate synthase that is derived from *Bacillus subtilis*. The activity of citrate synthase can also be modulated (e.g., decreased) by replacing the endogenous citrate synthase gene promoter with a synthetic constitutively low expressing promoter. The decrease of the activity of citrate synthase can result in more carbon flux into the mevalonate dependent biosynthetic pathway in comparison to microorganisms that do not have decreased expression of citrate synthase.

Pathways Involving Phosphotransacetylase and/or Acetate Kinase

Phosphotransacetylase (pta) (Shimizu et al. 1969. Biochim. Biophys. Acta 191: 550-558) catalyzes the reversible conversion between acetyl-CoA and acetylphosphate (acetyl-P), while acetate kinase (ackA) (Kakuda, H. et al. 1994. J. Biochem. 11:916-922) uses acetyl-P to form acetate. These genes can be transcribed as an operon in *E. coli*. Together, they catalyze the dissimilation of acetate, with the release of ATP. Thus, one of skill in the art can increase the amount of available acetyl Co-A by attenuating the activity of phosphotransacetylase gene (e.g., the endogenous phosphotransacetylase gene) and/or an acetate kinase gene (e.g., the endogenous acetate kinase gene). One way of achieving attenuation is by deleting phosphotransacetylase (pta) and/or acetate kinase (ackA). This can be accomplished by replacing one or both genes with a chloramphenicol cassette followed by looping out of the cassette. Acetate is produced by *E. coli* for a variety of reasons (Wolfe, A. 2005. Microb. Mol. Biol. Rev. 69:12-50). Without being bound by theory, since ackA-pta use acetyl-CoA, deleting those genes might allow carbon not to be diverted into acetate and to increase the yield of mevalonate or isoprene.

In some aspects, the recombinant microorganism produces decreased amounts of acetate in comparison to microorganisms that do not have attenuated endogenous phosphotransacetylase gene and/or endogenous acetate kinase gene expression. Decrease in the amount of acetate produced can be measured by routine assays known to one of skill in the art. The amount of acetate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of phosphotransacetylase (pta) and/or acetate kinase (ackA) can also be decreased by other molecular manipulation of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphotransacetylase gene and/or the endogenous acetate kinase gene results in more carbon flux into the mevalonate dependent biosynthetic pathway in comparison to microorganisms that do not have attenuated endogenous phosphotransacetylase gene and/or endogenous acetate kinase gene expression.

Pathways Involving Lactate Dehydrogenase

In *E. coli*, D-Lactate is produced from pyruvate through the enzyme lactate dehydrogenase (ldhA—FIG. 5) (Bunch, P. et al. 1997. Microbiol. 143:187-195). Production of lactate is accompanied with oxidation of NADH, hence lactate is produced when oxygen is limited and cannot accommodate all the reducing equivalents. Thus, production of lactate could be a source for carbon consumption. As such, to improve carbon flow through to mevalonate production (and isoprene), one of skill in the art can modulate the activity of lactate dehydrogenase, such as by decreasing the activity of the enzyme.

Accordingly, in one aspect, the activity of lactate dehydrogenase can be modulated by attenuating the activity of an endogenous lactate dehydrogenase gene. Such attenuation can be achieved by deletion of the endogenous lactate dehydrogenase gene. Other ways of attenuating the activity of lactate dehydrogenase gene known to one of skill in the art may also be used. By manipulating the pathway that involves lactate dehydrogenase, the recombinant microorganism produces decreased amounts of lactate in comparison to microorganisms that do not have attenuated endogenous lactate dehydrogenase gene expression. Decrease in the amount of lactate produced can be measured by routine assays known to one of skill in the art. The amount of lactate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of lactate dehydrogenase can also be decreased by other molecular manipulations of the enzyme. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Accordingly, in some cases, attenuation of the activity of the endogenous lactate dehydrogenase gene results in more carbon flux into the mevalonate dependent biosynthetic pathway in comparison to microorganisms that do not have attenuated endogenous lactate dehydrogenase gene expression.

Pathways Involving Malic enzyme

Malic enzyme (in *E. coli* sfcA and maeB) is an anaplerotic enzyme that catalyzes the conversion of malate into pyruvate (using NAD+ or NADP+) by the equation below:

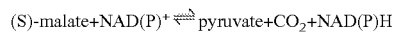

(S)-malate+NAD(P)$^+$ $\rightleftharpoons$ pyruvate+CO$_2$+NAD(P)H

Thus, the two substrates of this enzyme are (S)-malate and NAD(P)$^+$, whereas its 3 products are pyruvate, CO$_2$, and NADPH.

Expression of the NADP-dependent malic enzyme (maeB—FIG. 5) (Iwikura, M. et al. 1979. J. Biochem. 85: 1355-1365) can help increase mevalonate and isoprene yield by 1) bringing carbon from the TCA cycle back to pyruvate, direct precursor of acetyl-CoA, itself direct precursor of the mevalonate pathway and 2) producing extra NADPH which could be used in the HMG-CoA reductase reaction (Oh, M K et al. (2002) *J. Biol. Chem.* 277: 13175-13183; Bologna, F. et al. (2007) *J Bact.* 189:5937-5946).

As such, more starting substrate (pyruvate or acetyl-CoA) for the downstream production of mevalonate or isoprene can be achieved by modulating, such as increasing, the activity and/or expression of malic enzyme. The NADP-dependent malic enzyme gene can be an endogenous gene. One non-limiting way to accomplish this is by replacing the endogenous NADP-dependent malic enzyme gene promoter with a synthetic constitutively expressing promoter. Another non-limiting way to increase enzyme activity is by using one or more heterologous nucleic acids encoding an NADP-dependent malic enzyme polypeptide. One of skill in the art can monitor the expression of maeB RNA during fermentation or culturing using readily available molecular biology techniques.

Accordingly, in some embodiments, the recombinant microorganism produces increased amounts of pyruvate in comparison to microorganisms that do not have increased expression of an NADP-dependent malic enzyme gene. In some aspects, increasing the activity of an NADP-dependent malic enzyme gene results in more carbon flux into the mevalonate dependent biosynthetic pathway in comparison to microorganisms that do not have increased NADP-dependent malic enzyme gene expression.

Increase in the amount of pyruvate produced can be measured by routine assays known to one of skill in the art. The amount of pyruvate increase can be at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of malic enzyme can also be increased by other molecular manipulations of the enzyme. The increase of enzyme activity can be any amount of increase of specific activity or total activity as compared to when no manipulation has been effectuated. In some instances, the increase of enzyme activity is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Pathways Involving Pyruvate Dehydrogenase Complex

The pyruvate dehydrogenase complex, which catalyzes the decarboxylation of pyruvate into acetyl-CoA, is composed of the proteins encoded by the genes aceE, aceF and 1pdA. Transcription of those genes is regulated by several regulators. Thus, one of skill in the art can increase acetyl-CoA by modulating the activity of the pyruvate dehydrogenase complex. Modulation can be to increase the activity and/or expression (e.g., constant expression) of the pyruvate dehydrogenase complex. This can be accomplished by different ways, for example, by placing a strong constitutive promoter, like PL.6(aattcatataaaaaacatacagataac-catctgcggtgataaattatctctggcg-gtgttgacataaataccactggcggtgatactgagcacatca gcaggacgcact-gaccaccatgaaggtg (SEQ ID NO:1)- lambda promoter, GenBank NC_001416), in front of the operon or using one or more synthetic constitutively expressing promoters.

Accordingly, in one aspect, the activity of pyruvate dehydrogenase is modulated by increasing the activity of one or more genes of the pyruvate dehydrogenase complex consisting of (a) pyruvate dehydrogenase (E1), (b) dihydrolipoyl transacetylase, and (c) dihydrolipoyl dehydrogenase. It is understood that any one, two or three of these genes can be manipulated for increasing activity of pyruvate dehydrogenase. In another aspect, the activity of the pyruvate dehydrogenase complex can be modulated by attenuating the activity of an endogenous pyruvate dehydrogenase complex repressor gene, further detailed below. The activity of an endogenous pyruvate dehydrogenase complex repressor can be attenuated by deletion of the endogenous pyruvate dehydrogenase complex repressor gene.

In some cases, one or more genes of the pyruvate dehydrogenase complex are endogenous genes. Another way to increase the activity of the pyruvate dehydrogenase complex is by introducing into the microorganism one or more heterologous nucleic acids encoding one or more polypeptides from the group consisting of (a) pyruvate dehydrogenase (E1), (b) dihydrolipoyl transacetylase, and (c) dihydrolipoyl dehydrogenase.

By using any of these methods, the recombinant microorganism can produce increased amounts of acetyl Co-A in comparison to microorganisms wherein the activity of pyruvate dehydrogenase is not modulated. Modulating the activity of pyruvate dehydrogenase can result in more carbon flux into the mevalonate dependent biosynthetic pathway in comparison to microorganisms that do not have modulated pyruvate dehydrogenase expression.

Combinations of Mutations

It is understood that for any of the enzymes and/or enzyme pathways described herein, molecular manipulations that modulate any combination (two, three, four, five or six) of the enzymes and/or enzyme pathways described herein is expressly contemplated. For ease of the recitation of the combinations, citrate synthase (gltA) is designated as A, phosphotransacetylase (ptaB) is designated as B, acetate kinase (ackA) is designated as C, lactate dehydrogenase (ldhA) is designated as D, malic enzyme (sfcA or maeB) is designated as E, and pyruvate decarboxylase (aceE, aceF, and/or lpdA) is designated as F. As discussed above, aceE, aceF, and/or lpdA enzymes of the pyruvate decarboxylase complex can be used singly, or two of three enzymes, or three of three enzymes for increasing pyruvate decarboxylase activity.

Accordingly, for combinations of any two of the enzymes A-F, non-limiting combinations that can be used are: AB, AC, AD, AE, AF, BC, BD, BE, BF, CD, CE, CF, DE, DF and EF. For combinations of any three of the enzymes A-F, non-limiting combinations that can be used are: ABC, ABD, ABE, ABF, BCD, BCE, BCF, CDE, CDF, DEF, ACD, ACE, ACF, ADE, ADF, AEF, BDE, BDF, BEF, and CEF. For combinations of any four of the enzymes A-F, non-limiting combinations that can be used are: ABCD, ABCE, ABCF, ABDE, ABDF, ABEF, BCDE, BCDF, CDEF, ACDE, ACDF, ACEF, BCEF, BDEF, and ADEF. For combinations of any five of the enzymes A-F, non-limiting combinations that can be used are: ABCDE, ABCDF, ABDEF, BCDEF, ACDEF, and ABCEF. In another aspect, all six enzyme combinations are used: ABCDEF.

Accordingly, the recombinant microorganism as described herein can achieve increased mevalonate production that is increased compared to microorganisms that are not grown under conditions of tri-carboxylic acid (TCA) cycle activity, wherein metabolic carbon flux in the recombinant microorganism is directed towards mevalonate production by modulating the activity of one or more enzymes from the group consisting of (a) citrate synthase, (b) phosphotransacetylase and/or acetate kinase, (c) lactate dehydrogenase, (d) malic enzyme, and (e) pyruvate decarboxylase complex.

Other Regulators and Factors for Increased Production

Other molecular manipulations can be used to increase the flow of carbon towards mevalonate and/or isoprene production. One method is to reduce, decrease or eliminate the effects of negative regulators for pathways that feed into the mevalonate pathway. For example, in some cases, the genes aceEF-lpdA are in an operon, with a fourth gene upstream pdhR. pdhR is a negative regulator of the transcription of its operon. In the absence of pyruvate, it binds its target promoter and represses transcription. It also regulates ndh and cyoABCD in the same way (Ogasawara, H. et al. 2007. J. Bact. 189:5534-5541). In one aspect, deletion of pdhR regulator can improve the supply of pyruvate, and hence the production of mevalonate and isoprene.

In other aspects, the introduction of 6-phosphogluconolactonase (PGL) into microorganisms (such as various $E.\ coli$ strains) which lack PGL can be used to improve production of mevalonate and/or isoprene. PGL may be introduced using chromosomal integration or extra-chromosomal vehicles, such as plasmids.

Exemplary Cell Culture Media and Conditions

The invention also includes a cell or a population of cells in culture that produce isoprene. By "cells in culture" is meant two or more cells in a solution (e.g., a cell medium) that allows the cells to undergo one or more cell divisions. "Cells in culture" do not include plant cells that are part of a living, multicellular plant containing cells that have differentiated into plant tissues. In various aspects, the cell culture includes at least or about 10, 20, 50, 100, 200, 500, 1,000, 5,000, 10,000 or more cells.

Carbon source that can be used to cultivate the host cells are described in WO 2009/076676, WO 2010/003007, and WO 2009/132220. In one aspect, the recombinant cells of the invention can be grown in a fed-batch culture at the 15-L scale using the following reagents:

1000× Trace Metal Solution (per liter): Citric Acids*$H_2O$ 40 g, $MnSO_4$*$H_2O$ 30 g, NaCl 10 g, $FeSO4$*$7H_2O$ 1 g, $CoCl_2$*$6H_2O$ 1 g, $ZnSO$*$7H_2O$ 1 g, $CuSO_4$*$5H_2O$ 100 mg, $H_3BO_3$ 100 mg, $NaMoO_4$*$2H_2O$ 100 mg. Each component was dissolved one at a time in Di $H_2O$, pH was adjusted to 3.0 with HCl/NaOH, and then the solution was q.s. to volume and filter sterilized with a 0.22 micron filter.

Vitamin Solution (per liter): Thiamine hydrochloride 1.0 g, D-(+)-biotin 1.0 g, nicotinic acid 1.0 g, D-pantothenic acid 4.8 g, pyridoxine hydrochloride 4.0 g. Each component was dissolved one at a time in Di $H_2O$, pH was adjusted to 3.0 with HCl/NaOH, and then the solution was q.s. to volume and filter sterilized with 0.22 micron filter.

Macro Salt Solution (per liter): $MgSO_4$*$7H_2O$ 296 g, citric acid monohydrate 296 g, ferric ammonium citrate 49.6 g. All components were dissolved in water, q.s. to volume and filter sterilized with 0.22 micron filter.

Feed solution (per kilogram): Glucose 0.57 kg, Di $H_2O$ 0.38 kg, $K_2HPO_4$ 7.5 g, and 100% Foamblast 10 g. All components were mixed together and autoclaved. Macro Salt Solution 11.1 mL, 1000× Trace Metal Solution 1.6 ml, Vitamin Solution 13.1 mL and 5.4 mL of a 350 g/L yeast extract solution (filter sterilized with 0.22 micron filter) were added after the solution had cooled to 25° C.

Phosphate Solution (per liter): $KH_2PO_4$ 68 g, $K_2HPO_4$ 68 g. All components were dissolved in water, q.s. to volume and autoclaved for 30 min.

Other methods and materials that can be used for culturing any of the recombinant cells herein is described in the Examples. Materials and methods suitable for the maintenance and growth of bacterial cultures are well known in the art. Exemplary techniques may be found in WO 2009/076676, WO 2010/003007, and WO 2009/132220, and *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass. In some aspects, the cells are cultured in a culture medium under conditions permitting the expression of one or both of the IspG enzymes, one or more isoprene synthase polypeptide, iron-sulfur cluster-interacting redox polypeptide, DXP pathway polypeptide, DXP pathway associated polypeptide, or IDI polypeptide encoded by a nucleic acid inserted into the host cells.

Exemplary Methods for Decoupling Isoprene Production from Cell Growth.

The recombinant cells of the invention can be grown in a way as to decouple the isoprene production from cell growth. When feedstock is used, it is desirable for the carbon from the feedstock to be converted to isoprene rather than to the growth and maintenance of the cells. In some aspects, the cells are grown to a low to medium $OD_{600}$, then production of isoprene is started or increased. This strategy permits a large portion of the carbon to be converted to isoprene. One of skill in the art can grow the recombinant cells of the invention by following the teaching in WO 2010/003007.

In some aspects, isoprene is only produced in stationary phase. In some aspects, isoprene is produced in both the growth phase and stationary phase. In some aspects, isoprene is only produced in the growth phase. In some aspects, the nucleic acids encoding the various enzymes and polypeptides described herein are placed under the control of a promoter or factor that is more active in stationary phase than in the growth phase. For example, one or more isoprene synthase nucleic acid, iron-sulfur cluster-interacting redox nucleic acid, DXP pathway nucleic acid, DXP pathway associated nucleic acid, IspG enzymes and/or IDI nucleic acid may be placed under control of a stationary phase sigma factor, such as RpoS. In some aspects, one or more isoprene synthase nucleic acid, iron-sulfur cluster-interacting redox nucleic acid, DXP pathway nucleic acid, DXP pathway associated nucleic acid, IspG enzymes and/or IDI nucleic acid are placed under control of a promoter inducible in stationary phase, such as a promoter inducible by a response regulator active in stationary phase.

Production of Isoprene within Safe Operating Ranges

The production of isoprene using the recombinant cells disclosed herein can be done within safe operating levels according to its flammability characteristics, which simplifies the design and construction of commercial facilities, vastly improves the ability to operate safely, and limits the potential for fires to occur. In particular, the optimal ranges for the production of isoprene are within the safe zone, i.e., the nonflammable range of isoprene concentrations. In one such aspect, the invention features a method for the production of isoprene within the nonflammable range of isoprene concentrations (outside the flammability envelope of isoprene). Safe operating ranges are described in WO 2010/003007 and the ranges disclosed therein are specifically incorporated by reference.

Exemplary Production of Isoprene

The invention provides, inter alia, compositions and methods for increasing the production of isoprene from cultured cells using two types of IspG enzymes, one or more DXP pathway enzymes and isoprene synthase, optionally in combination with iron-sulfur cluster-interacting redox genes or polypeptides and IDI genes and polypeptides. In some aspects, the recombinant cells produce a cumulative titer (total amount) of isoprene at greater than or about 1, 2, 3, 4, 5, 6, 7, 8, 8.4, 9, 10, 25, 50, 75, 100, 150, 175, or 200 $g/L_{broth}$. In some aspects, the upper limit is about 1, 2, 3, 4, 5, 6, 7, 8, 8.4, 9, 10, 25, 50, 75, 100, 150, 175, or 200 $g/L_{broth}$.

Various measurement for isoprene production (e.g., specific productivity of isoprene, instantaneous isoprene production rate in a fermentor, etc.) can be measured as disclosed in WO 2009/076676, WO 2010/003007, and WO 2009/132220.

In some aspects, the isoprene composition comprises greater than or about 99.90, 99.92, 99.94, 99.96, 99.98, or 100% isoprene by weight compared to the total weight of all C5 hydrocarbons in the composition. In some aspects, the composition has a relative detector response of greater than or about 99.90, 99.91, 99.92, 99.93, 99.94, 99.95, 99.96, 99.97, 99.98, 99.99, or 100% for isoprene compared to the detector response for all C5 hydrocarbons in the composition. In some aspects, the isoprene composition comprises between about 99.90 to about 99.92, about 99.92 to about 99.94, about 99.94 to about 99.96, about 99.96 to about 99.98, about 99.98 to 100% isoprene by weight compared to the total weight of all C5 hydrocarbons in the composition.

In some aspects, the isoprene composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such as 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, or cis-pent-3-ene-1-yne) by weight compared to the total weight of all C5 hydrocarbons in the composition. In some aspects, the composition has a relative detector response of less than or about 0.12, 0.10, 0.08, 0.06, 0.04, 0.02, 0.01, 0.005, 0.001, 0.0005, 0.0001, 0.00005, or 0.00001% for C5 hydrocarbons other than isoprene compared to the detector response for all C5 hydrocarbons in the composition. In some aspects, the composition has a relative detector response of less than or about 0.12, 0.10, 0.08, 0.06, 0.04, 0.02, 0.01, 0.005, 0.001, 0.0005, 0.0001, 0.00005, or 0.00001% for 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, or cis-pent-3-ene-1-yne compared to the detector response for all C5 hydrocarbons in the composition. In some aspects, the isoprene composition comprises between about 0.02 to about 0.04%, about 0.04 to about 0.06%, about 0.06 to 0.08%, about 0.08 to 0.10%, or about 0.10 to about 0.12% C5 hydrocarbons other than isoprene (such as 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, or cis-pent-3-ene-1-yne) by weight compared to the total weight of all C5 hydrocarbons in the composition.

In some aspects, the isoprene composition comprises less than or about 50, 40, 30, 20, 10, 5, 1, 0.5, 0.1, 0.05, 0.01, or 0.005 ug/L of a compound that inhibits the polymerization of isoprene for any compound in the composition that inhibits the polymerization of isoprene. In some aspects, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a compound that inhibits the polymerization of isoprene for any compound in the composition that inhibits the polymerization of isoprene. In some aspects, the isoprene composition comprises less than or about 50, 40, 30, 20, 10, 5, 1, 0.5, 0.1, 0.05, 0.01, or 0.005 ug/L of a hydrocarbon other than isoprene (such as 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, or cis-pent-3-ene-1-yne). In some aspects, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a hydrocarbon other than isoprene. In some aspects, the isoprene composition comprises less than or about 50, 40, 30, 20, 10, 5, 1, 0.5, 0.1, 0.05, 0.01, or 0.005 ug/L of a protein or fatty acid (such as a protein or fatty acid that is naturally associated with natural rubber).

In some aspects, the isoprene composition comprises less than or about 10, 5, 1, 0.8, 0.5, 0.1, 0.05, 0.01, or 0.005 ppm of alpha acetylenes, piperylenes, acetonitrile, or 1,3-cyclopentadiene. In some aspects, the isoprene composition comprises less than or about 5, 1, 0.5, 0.1, 0.05, 0.01, or 0.005 ppm of sulfur or allenes. In some aspects, the isoprene composition comprises less than or about 30, 20, 15, 10, 5, 1, 0.5, 0.1, 0.05, 0.01, or 0.005 ppm of all acetylenes (such as pentyne-1, butyne-2, 2 MB1-3yne, and 1-pentyne-4-yne). In some aspects, the isoprene composition comprises less than or about 2000, 1000, 500, 200, 100, 50, 40, 30, 20, 10, 5, 1, 0.5, 0.1, 0.05, 0.01, or 0.005 ppm of isoprene dimers, such as cyclic isoprene dimmers (e.g., cyclic C10 compounds derived from the dimerization of two isoprene units).

In some aspects, the composition comprises greater than about 2 mg of isoprene, such as greater than or about 5, 10, 20, 30, 40, 50, 60, 70, 80, 90, 100, 200, 300, 400, 500, 600, 700, 800, 900, or 1000 mg of isoprene. In some aspects, the composition comprises greater than or about 2, 5, 10, 20, 30, 40, 50, 60, 70, 80, 90, 100 g of isoprene. In some aspects, the amount of isoprene in the composition is between about 2 to about 5,000 mg, such as between about 2 to about 100 mg, about 100 to about 500 mg, about 500 to about 1,000 mg, about 1,000 to about 2,000 mg, or about 2,000 to about 5,000 mg. In some aspects, the amount of isoprene in the composition is between about 20 to about 5,000 mg, about 100 to about 5,000 mg, about 200 to about 2,000 mg, about 200 to about 1,000 mg, about 300 to about 1,000 mg, or about 400 to about 1,000 mg. In some aspects, greater than or about 20, 25, 30, 40, 50, 60, 70, 80, 90, or 95% by weight of the volatile organic fraction of the composition is isoprene.

Exemplary Isoprene Purification Methods

In some aspects, any of the methods described herein further include recovering the isoprene. For example, the isoprene produced using the compositions and methods of the invention can be recovered using standard techniques, such as gas stripping, membrane enhanced separation, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In one aspect, the isoprene is recovered by absorption stripping (see, e.g., US Pub. No. 2011/0178261). In particular, aspects, extractive distillation with an alcohol (such as ethanol, methanol, propanol, or a combination thereof) is used to recover the isoprene. In some aspects, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation (such as condensation due to exposure to a condensation coil or do to an increase in pressure). In some aspects, membrane enrichment of a dilute isoprene vapor stream above the dew point of the vapor resulting in the condensation of liquid isoprene. In some aspects, the isoprene is compressed and condensed.

The recovery of isoprene may involve one step or multiple steps. In some aspects, the removal of isoprene vapor from the fermentation off-gas and the conversion of isoprene to a liquid phase are performed simultaneously. For example, isoprene can be directly condensed from the off-gas stream to form a liquid. In some aspects, the removal of isoprene vapor from the fermentation off-gas and the conversion of isoprene to a liquid phase are performed sequentially. For example, isoprene may be adsorbed to a solid phase and then extracted from the solid phase with a solvent. In one aspect, the isoprene is recovered by using absorption stripping as described in U.S. application Ser. No. 12/969,440 (US Publ. No. 2011/0178261).

In some aspects, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some aspects, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. In some aspects, the isoprene is at least about 20%, by weight, free from other components that are present when the isoprene is produced. In various aspects, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

In some aspects, at least a portion of the gas phase remaining after one or more recovery steps for the removal of isoprene is recycled by introducing the gas phase into a cell culture system (such as a fermentor) for the production of isoprene.

EXAMPLES

The examples, which are intended to be purely exemplary of the invention and should therefore not be considered to limit the invention in any way, also describe and detail aspects and aspects of the invention discussed above. Unless indicated otherwise, temperature is in degrees Centigrade and pressure is at or near atmospheric. The foregoing examples and detailed description are offered by way of illustration and not by way of limitation. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1

Generation of Ptac Anabaena ispH-T elong ispG System aspA term/pEWL454

Cloning of the *T. elongatus* IspG System into Ptac Anabaena ispH aspA term/pEWL454

A DNA sequence harboring the T. elongates IspG system consisting of gcpE-petF-petH present in plasmid Ptac-gcpE-petF-petH/pK184 has been described previously (see U.S.

patent application Ser. No. 12/817,134 (US Publ. No. 2011/0014672), Example 9). Using DNA Polymerase I (Large Klenow Fragment), BamHI, and PstI (New England BioLabs, MA) a 5' blunt (BamHI destroyed)-3' PstI gcpE-petF-petH fragment was obtained. The Ptac Anabaena ispH aspA term/pEWL454 vector was digested with SmaI and PstI (New England BioLabs, MA) according to the manufacturer's suggested protocol. The SmaI and PstI cut Ptac Anabaena ispH aspA term/pEWL454 DNA was combined with the final digest reaction harboring the 5' blunt (BamHI destroyed)-gcpE-petF-petH-3' PstI fragment and the DNA mixture cleaned using a Qiagen QiaQuick Gel Extraction Kit. Approximately one half of the cleaned cut DNA was ligated using T4 DNA Ligase (New England Biolabs, MA) according to the manufacturer's suggested protocol. A portion of the ligation was used to transform strain MD09-220, previously described in U.S. patent application Ser. No. 12/817,134 (US Publ. No. 2011/0014672), example 11, by electroporation methods. The Bio Rad Gene Pulser system (Bio-Rad, CA) with a 0.1 cm cuvette, cat. #165-2089, and a transformation protocol suggested by the manufacturer was used. Transformants were recovered in LB broth plus 500 uM mevalonic acid for 1 hour at 37° C. before plating onto LB agar containing kanamycin (50 ug/ml) without mevalonic acid. Only transformants harboring a functionally expressed ispH allele were expected to form colonies. Kanamycin resistant colonies were selected for verification of the gcpE-petF-petH insert as follows:

A polymerase chain reaction (PCR) assay was setup by preparation of the following mixture;
0.5 μl template (approx. 0.5 ul volume of colony cells)
16.25 μl diH2O
0.25 μl dNTP's (100 mM)
0.625 μl primer (10 uM) 5' top Te gcpE seq primer
0.625 μl primer (10 uM) 5' NdeI F— T.e. gcpE pET-15b
0.625 μl primer (10 uM) 3' bottom Te gcpE seq primer
0.625 μl primer (10 uM) 3' BamHI R— T.e. gcpE pET-15b
5.0 μl HerculaseII Buffer
0.5 μl of HerculaseII fusion (Stratagene, CA)
25 μl total volume The PCR reaction was run on a Biometra T3000 Combi Thermocycler (Biometra, Germany) using the following cycle parameters: 95° C.×2 min., (95° C.×30 sec., 55° C.×30 sec., 72° C.×1 min.)×29 cycles; 72° C.×5 min., 4° C. until cool.

```
Primer sequences were as follows;
5' top Te gcpE seq primer:
5' - cacttgagtttatacgcatc
(SEQ ID NO: 2)

3' bottom Te gcpE seq primer:
5' - gatgcgtataaactcaagtg
(SEQ ID NO: 3)

5' NdeI F- T.e. gcpE pET-15b:
5' - gcggcagccatatgcaaacgttgccaagccca
(SEQ ID NO: 4)

3' BamHI R- T.e. gcpE pET-15b:
5' - tagcagccggatccttatggatctacccatctacc
(SEQ ID NO: 5)
```

The resulting PCR fragments were separated on a 1.2% E-gel (Invitrogen, CA). Colonies from which a PCR product(s) of anticipated size was observed were considered positive for the gcpE-containing insert and processed further.

Kanamycin resistant colonies from which a successful fragment of gcpE was amplified were grown overnight in LB broth containing kanamycin (50 ug/ml), and harvested for subsequent plasmid preparation. Plasmid constructs were isolated using Qiagen Qiaprep Spin Miniprep Kit (Qiagen, CA). Plasmid preparations of interest were sequenced (Sequetech, CA) using primers M13-65(5'-AGGCGATTAAGT-TGGGTA) (SEQ ID NO:6)) and pSE3805(5'-GGCTCG-TATAATGTGTGG) (SEQ ID NO:7)) to further verify insertion of the gcpE-petF-petH sequence into Ptac Anabaena ispH aspA term/pEWL454, with the resulting plasmid construct now referred to as Ptac Anabaena ispH-T elong ispG system aspA term/pEWL454(see FIG. 1). A correct Ptac Anabaena ispH-T elong ispG system aspA term/pEWL454 clone was identified and was designated as strain REM I6_17.

Example 2

Generation of the Enhanced DXP Flux Isoprene Producing Strain REM F2_18

Transformation of REM I7_11 with Ptac Anabaena ispH-T elong ispG System aspA term/pEWL454

The isoprene producing parental strain REM I7_11 was described previously (see U.S. patent application Ser. No. 12/817,134 (US Publ. No. 2011/0014672), Example 29). In addition to increased expression from chromosomally encoded DXP pathway genes dxs and dxr, the REM I7_11 strain harbors plasmid encoded copies of both fldA and ispG as well as the fldA and ispG loci present within the BL21 genome. The Ptac Anabaena ispH-T elong ispG system aspA term/pEWL454 plasmid was introduced by electroporation into strain REM I7_11. Electroporation was performed using a Bio-Rad Gene Pulser system with a 0.1 cm cuvette, cat. #165-2089. Transformation was achieved by following the manufacturer's suggested protocol. Transformants were recovered in LB broth for 1 hour at 37° C. before plating onto LB agar containing spectinomycin (50 ug/ml), carbenicillin (50 ug/ml), and kanamycin (50 ug/ml). The resulting strain was named REM F2_18.

Example 3

Large Scale Fermentation of REM F2_18 Yielding an 8.4 g/L Isoprene Titer

Isoprene production from E. coli cells expressing genes from the DXP pathway and isoprene synthase were grown in fed-batch culture at the 15-L scale using the following reagents;

1000× Trace Metal Solution (per liter): Citric Acids*$H_2O$ 40 g, $MnSO_4$*$H_2O$ 30 g, NaCl 0 g, $FeSO4$*$7H_2O$ 1 g, $CoCl_2$*$6H_2O$ 1 g, $ZnSO$*$7H_2O$ 1 g, $CuSO_4$*$5H_2O$ 100 mg, $H_3BO_3$ 100 mg, $NaMoO_4$*$2H_2O$ 100 mg. Each component was dissolved one at a time in Di $H_2O$, pH was adjusted to 3.0 with HCl/NaOH, and then the solution was q.s. to volume and filter sterilized with a 0.22 micron filter.

Vitamin Solution (per liter): Thiamine hydrochloride 1.0 g, D-(+)-biotin 1.0 g, nicotinic acid 1.0 g, D-pantothenic acid 4.8 g, pyridoxine hydrochloride 4.0 g. Each component was dissolved one at a time in Di $H_2O$, pH was adjusted to 3.0 with HCl/NaOH, and then the solution was q.s. to volume and filter sterilized with 0.22 micron filter.

Macro Salt Solution (per liter): $MgSO_4$*$7H_2O$ 296 g, citric acid monohydrate 296 g, ferric ammonium citrate 49.6 g. All components were dissolved in water, q.s. to volume and filter sterilized with 0.22 micron filter.

Feed solution (per kilogram): Glucose 0.57 kg, Di $H_2O$ 0.38 kg, $K_2HPO_4$ 7.5 g, and 100% Foamblast 10 g. All components were mixed together and autoclaved. Macro Salt Solution 11.1 mL, 1000× Trace Metal Solution 1.6 ml, Vitamin Solution 13.1 mL and 5.4 mL of a 350 g/L yeast extract solution (filter sterilized with 0.22 micron filter) were added after the solution had cooled to 25° C.

Phosphate Solution (per liter): $KH_2PO_4$ 68 g, $K_2HPO_4$ 68 g. All components were dissolved in water, q.s. to volume and autoclaved for 30 min.

Fermentation was performed in a 15-L bioreactor with the F2_18 strain; *E. coli* BL21 cells over expressing the first two enzymes in the dxp pathway (PL.6-dxs and GI1.6-dxr), the last enzyme in the DXP pathway (GI1.6-yIDI), other genes involved in the DXP pathway (GI1.6-fldA-ispG/pCL, PTac-Anabaena ispH-T.elong.gcpE-petF-petH aspA term/ pEWL454), the lower MVA pathway (PL.2-mKKDyI), truncated isoprene synthase from *P. alba* (pDW33, see U.S. Publ No. 2011/0014672), and containing a restored chromosomal pgl gene (t ybgS::Kan or t ybgS::frt). This experiment was carried out at pH 7.0 and 34° C. Truncated isoprene synthase is also described in US Patent Publication No. 2010/0003716.

A frozen vial of the *E. coli* strain was thawed and inoculated into tryptone-yeast extract medium for the bioreactor. After the culture grew to optical density 1.0, measured at 550 nm ($OD_{550}$), 500 mL was used to inoculate a 15-L bioreactor and bring the initial tank volume to 5 L. Carbenicillin, spectinomycin and kanamycin were each present at a concentration of 50 ug/mL, respectively, in the seed flask and fermentation tank.

Once the batch glucose was depleted, the glucose feed solution was fed at an exponential rate from 0.35 g/min until the feed rate reached 2.72 g/min. This was immediately followed by a linear ramp that lasted the duration of the fermentation and brought the feed rate up to 4.225 g/min at 68 h. The total amount of glucose delivered to the bioreactor during the 68 hr fermentation was 3.5 kg.

The phosphate solution described above was fed at 0.21 g/min starting at a carbon dioxide evolution rate (CER) of 50 mmol/L/h, and at 16 h feed time, was stepped down to 0.11 g/min and fed for the duration of the experiment.

Induction was achieved by adding isopropyl-beta-D-1-thiogalactopyranoside (IPTG) from a 10 mg/mL stock. At time zero, 3 mL was added (25 uM). Subsequent additions were at a carbon dioxide evolution rate (CER) of 25 mmol/L/h (3 mL), CER of 50 mmol/L/h (6 mL), CER of 100 mmol/L/h (6 mL) and CER of 150 mmol/L/h (3 mL).

Figure 2:
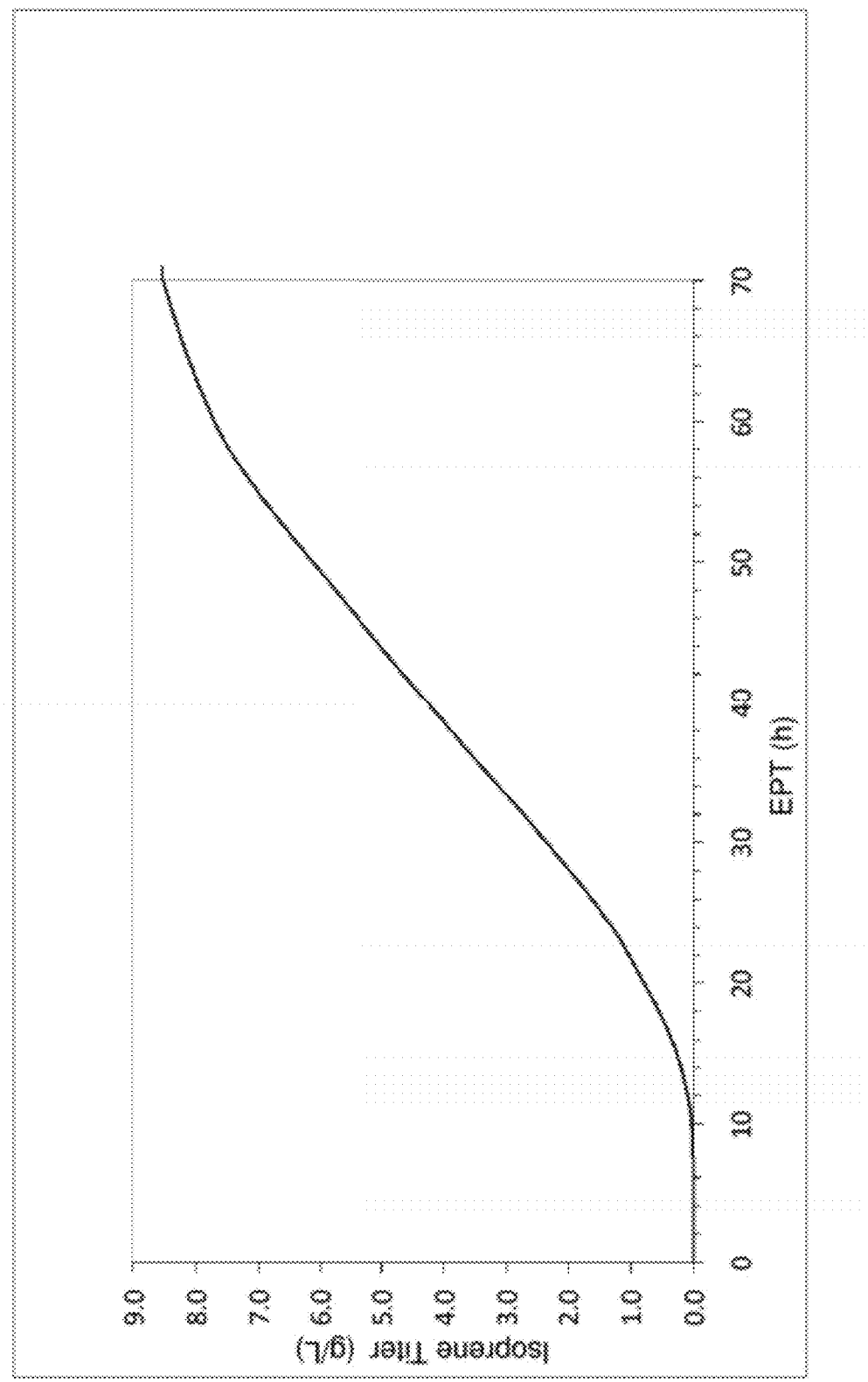
FIG. 2 shows a graph of isoprene titer versus time in a 15 L scale fermentation of REM F2__18.

The isoprene level in the off-gas from the bioreactors was determined using a Hiden Analytical mass spectrometer (Livonia, Mich., USA). Calibration of the instrument was done with an isoprene calibration standard supplied by Precision Gas Products Inc. (Mississauga, Ontario, Canada). The isoprene titer increased over the course of the fermentation to a maximum value of 8.4 g/L at 68 hr (see FIGS. 2 and 4).

Equation for Calculating Isoprene Titer:

$$\int (\text{Instantaneous isoprene production rate, g/L/hr})dt$$
from $t=0$ to 68 hrs [=] g/L broth Sequence of Plasmid Ptac Anabaena ispH-T elong ispG System aspA term/pEWL454

```
cgataagctagcttcacgctgccgcaagcactcagggcgcaagggctgctaaaggaagcggaacacgtagaaagccagtcc gcagaaacggtgctgaccccggatgaatgtcagctactgggctatctggacaaggggaaaacgcaagcgcaaagagaaagcaggtagcttgc agtgggcttacatggcgatagctagactgggcggttttatggacagcaagcgaaccggaattgccagctgggcgccctctggtaaggttggg aagccctgcaaagtaaactggatggctttcttgccgccaaggatctgatggcgcaggggatcaagatctgatcaagagacaggatgaggatcgt ttcgcatgattgaacaagatggattgcacgcaggttctccggccgcttgggtggagaggctattcggctatgactgggcacaacagacaatcgg ctgctctgatgccgccgtgttccggctgtcagcgcaggggcgcccggttcttttttgtcaagaccgacctgtccggtgccctgaatgaactccaag acgaggcagcgcggctatcgtggctggccacgacgggcgttccttgcgcagctgtgctcgacgttgtcactgaagcgggaagggactggctg ctattgggcgaagtgccggggcaggatctcctgtcatctcaccttgctcctgccgagaaagtatccatcatggctgatgcaatgcggcggctgca tacgcttgatccggctacctgcccattcgaccaccaagcgaaacatcgcatcgagcgagcacgtactcggatggaagccggtcttgtcgatcag gatgatctggacgaagagcatcaggggctcgcgccagccgaactgttcgccaggctcaaggcgcggatgcccgacggcgaggatctcgtcg tgacccatggcgatgcctgcttgccgaatatcatggtggaaaatggccgcttttctggattcatcgactgtgccggctgggtgtggcggaccgct atcaggacatagcgttggctacccgtgatattgctgaagagcttggcggcgaatgggctgaccgcttcctcgtgctttacggtatcgccgctcccg attcgcagcgcatcgccttctatcgccttcttgacgagttcttctgagcgggactctggggttcggatgataagctgtcaaacatgagaattacaact tatatcgtatggggctgacttcaggtgctacatttgaagagataaattgcactgaaatctagaaatattttatctgattaataagatgatcttcttgagat cgttttggtctgcgcgtaatctcttgctctgaaaacgaaaaaaccgccttgcagggcggttttttcgaaggttctctgagctaccaactctttgaaccg aggtaactggcttggaggagcgcagtcaccaaaacttgtcctttcagtttagccttaaccggcgcatgacttcaagactaactcctctaaatcaatta ccagtggctgctgccagtggtgcttttgcatgtctttccgggttggactcaagacgatagttaccggataaggcgcagcggtcggactgaacggg gggttcgtgcatacagtccagcttggagcgaactgcctacccggaactgagtgtcaggcgtggaatgagacaaacgcggccataacagcgga atgacaccggtaaaccgaaaggcaggaacaggagagcgcacgagggagccgcagggggaaacgcctggtatctttatagtcctgtcgggt ttcgccaccactgatttgagcgtcagatttcgtgatgcttgtcaggggggcggagcctatggaaaaacggctttgcctcctgcgttatcccctgatt ctgtggataaccgtattaccgcctttgagtgagctgataccgctcgccgcagccgaacgaccgagcgcagcgagtcagtgagcgaggaagcg gaagagcgcccaatacgcaaaccgcctctccccgcgcgttggccgattcattaatgcagctggcacgacaggtttcccgactggaaaggaattc
```

-continued

```
tgttgacaattaatcatcggctcgtataatgtgtggaattgtgagcggataacaatttcacacaggaaacagattacggatccctggagtttaaacat
atggatactaaaacctttaaacgtacgttgcaacactccgaaaactacaatcggaaagggttcggtcatcaggcggaggttgcaactcaactgca
atcagaatatcagagttctttgattcaggaaatccgcgatcgcaactacactcttcaacgtggggatgtcacgataagacttgctcaggcatttggct
tctgctggggtgttgaacgtgcggtcgcgatggcttatgagacccggaagcattttccaactgaacgcatctggattaccaacgaaatcattcaca
atccgagcgtcaaccagcggatgcaggaaatgcaagtgggctttataccagtagaggcgggcaacaaggattttagcgtagtcggcaataatg
acgtcgttatcctgccagcctttggcgcttctgtgcaagagatgcagcttttatctgaaaaaggatgtaaaatagttgataccacatgtccgtgggta
tcaaaagtctggaataccgtggaaaagcataaaaaggggggatcatacctctataatacatggcaaatataaacacgaagaaacgattgccacaa
gttccttcgcgggtaaatatctcatcgtccttaaccttaaggaagcacaatacgttgctgactacattctgcatgggggtaatcgtgaggagttcttac
agaaatttgcaaaagcatgctcggcgggctttgaccccgatagagatcttgaaagagttggcattgccaatcagacaacaatgttgaaaggaga
gaccgaacagatcggtaaacttttttgaacataccatgctgcaaaaatacggacccgtggagttaaatcaacattttcagtccttcaatacaatttgcg
acgctacccaggaacggcaggacgccatgctggagctggtacaagaaaatttggacctcatgatcgtgatcggaggttttaattcttccaacaca
acacagctccaacagattagccaggaacggggtctgccgtcctatcatattgatgtagttgagcgtattaaaagcataaactcgatagagcaccg
gcagttaaacgagagttggtcactacggaaaattggctgcctgcgggcaaaattgtcgtaggtgtaacaagtggcgcgagtacaccagataag
gtggttgaagacgtgatcgaaaagatctttgcgcttaaagcaacagcggccgtcttttaacccgatccatttgaggagtaagccatgcaaacgttg
ccaagcccagttcaagctacaccaacggaaacagctattgttagacgcaaaacccgcccggttccgataggctccgttgttattggtggcggcc
atcccgtggctgttcagtcaatgattaacgaagacactctggatatcgaaggttctgttgctgcaattcggcgcttacacgagatcggttgcgagat
cgtacgtgtgactgtaccttcattagcacacgcgaaagcaatggaagagattcgggatcggctttataaaacgtacaaaccggtcccccttagttgc
cgacgtgcatcataacggaatgaaaatcgcgttagaggttgccaagtacgtggacaatgtgcgcattaatcctggattatacgtgtttgagaagcc
aaaaccaaatcgcacggagtacactcaagctgaatttgacgagattggcgcgaaaatccgtgaaacgttggaaccactggtaatttcactgcgg
gatcagggaaagtcgatgcgcattggcgttaatcatggcagtctggcggaacggatgctgtttacctatggcgatacccagagggtatggtag
agagtgcacttgagtttatacgcatctgtgaaagtctcaacttctataacttagaaatttcccttaaagctagccgcgtcccggttatgatagccgcca
atcggcttatggttaagcgcatggacgagctgggtatggattatccgttgcatctcggagtgactgaggcaggtgatggtgaatatggccgtatta
aaagcacagcaggcattgcaacactgctggcggaaggaattggagacacaatccgtgtttcattgactgaagctccggaaaaggaaatccccg
tgtgctatggcatccttcaagccctcggtctccgccgcaccatggtagaatatgtagcttgcccgtcgtgtggtcggacattgtttaacctggaaga
ggttctgcacaaggtgagagaagcgactaaacacctgacgggactgaatattgcggttatgggatgtattgtaaatggacctggcgaaatggcc
gatgcagactacggctatgtaggtaaacagccgggatatataagtctttaccgcggccgggaagaagtcaagaaagtgcccgaggccgaggg
cgttgcagctctggtcgaactgataaaagcggatggtagatgggtagatccataagtggagctcccggtaccgtggacgaggtttaatatggc
gacgtataaagtcacactggtccgtccggatggcagcgaaacgaccatcgatgttccggaggacgaatacatactggatgtcgccgaagaaca
aggtctggatctcccgttttcttgtcgcgccggtgcctgctctacctgtgctggcaaattgttggagggagaagtcgatcaaagcgaccagagctt
cttggatgacgatcagatcgaaaaaggattcgtgcttacttgtgtggcctaccccgttcggactgcaagatcttgacgaaccaagaggaggagc
tgtactaagaggtcgacgacgcatgcattaacagaggttagtatgtataatgccactaactctcgctcacgtatgttccggtacgaagttgtgggc
tgcgccaaacggcggagacggagaaaacaaattacgcgatcagaaactctggctcgcagttctttaatgtgccttatgaccgcatgaaccagttt
atgcagcagatcactcggtggggcggtaaaattgtcagtattcagcccttaacggaaccgtggccccacttgctgcaaccacggagccagctg
ccaataacggagctgcacctgtgaaagaaaagaaagtcgatataccggtcaacatctaccgtcccaataatccctgcataggtaaggttattagc
aacgaggaactggtccggaaggcggtgagggtacggtgaaacatattatctttgatatatcggggaccgaattacgttacttggaagggcagt
caatcggtatcattcccgcgggcacggacgcgaacggtaaaccacataagctgcgtctgtattccattgcttccacaagacatggtgactttcagg
atgacaagacggtgtccttatgcgtacggagattagaatacaaagataaagagaccggggagaccatttatggcgtgtgcagttcgtatcttaatc
agttacagcctggagatgaagtcaaaatcacaggtcctgttgggaaagaaatgcttctctctgacgacccagaagcgactattattatgctggcta
ccggcactggaatagcgccatttcgggcatttttatggcggatgttcaaagagaacaacccggattaccagttcaaaggccttgcgtggctgttctt
tggcgtcgcttatactgccaatatcctgtataaggacgagcttgaagctatccaagcccagtatcccgatcattttcggttaacctacgcgatttccc
gtgaacaaaaaaccccggacggaggggaaaatgtacatccagggtcggatcgcagagcacgctgatgaaatctggcaactgctgcaaaagaa
```

-continued

```
aaacacccacgtgtacatgtgtggcctgcgtgggatggaacctggaatagacgaggccatgaccgcagcggccgcgaaaaacggagctgac tggcaggagtttctgaaaggtacgctgaaaaaggaaggcagatggcatgtcgaaacttattaactgcagtacaaataaaaaaggcacgtcagat gacgtgccttttttcttgaagcttggcactggccgtcgttttacaacgtcgtgactgggaaaaccctggcgttacccaacttaatcgccttgcagcac atcccccttcgccagctggcgtaatagcgaagaggcccgcaccgatcgcccttcccaacagttgcgcagcctgaatggcgaatggcg
(SEQ ID NO: 8)
```

Example 4

Large Scale Fermentation of REM H8_12

A plasmid-encoded *E. coli* IspG system (GI1.6-fldA-ispG/pCL) is combined with a plasmid-encoded *T. elongatus* IspG system (PTac-gcpE-petF-petH/pK185) into a DXP host strain. Comparisons are done for isoprene production at the 14-L scale using comparable fermentation processes to the *E. coli* IspG system alone strain REM H8_12 (control). Without being bound by theory, if the IspG activity is enhanced over the control strain and IspH activity is not limiting, then higher isoprene titer is generated by the combined *E. coli* and *T. elongatus* IspG systems strain.

Compatible expression constructs are generated using standard molecular biology techniques in order to accommodate the additional heterologous IspH enzyme expressed in this particular background while maintaining similar antibiotic resistance genes to the control strain as well as keeping a comparable copy-number of the genes of interest. The genes encoding the *T. elongatus* IspG system are combined with the gene encoding the additional heterologous IspH enzyme into one operon harbored on a pK184 vector derivative, pEWL454. This results in the vector construct PTac-Anabaena ispH-T. elong IspG system/pEWL454, kanamycin resistant.

The relevant test strain, REM F2_18, has the genotype: BL21 pgl+PL.2-lower MVA pathway GI1.6-yidi PL.6-dxs GI1.6-dxr+GI1.6-fldA-ispG/pCL (Spec 50)+PTac-Anabaena ispH-T. elong IspG system/pEWL454 (Kan 50)+PTrc-truncated alba IspS/pTrc His (Carb 50). The control strain is: BL21 pgl+PL.2-lower MVA pathway GI1.6-yidi PL.6-dxs GI1.6-dxr+GI1.6-fldA-ispG/pCL (Spec 50)+PTac Anabaena ispH/pK184 (Kan 50)+PTrc-truncated alba IspS/pTrc His (Carb 50).

Example 5

Altering IspG Levels for Enhanced In Vivo Activity

The expression of the *E. coli* IspG system is increased to levels greater than that in the current *E. coli* IspG system isoprene producing strain (control). The two strains are compared for isoprene production. Without being bound by theory, if the IspG activity is enhanced over the control strain and IspH activity is not limiting, then a higher isoprene titer is generated by the enhanced *E. coli* IspG system strain.

In order to increase the expression of the *E. coli* IspG system, molecular biology methods are used to either increase the expression of the *E. coli* IspG system from its current vector construct (pCL based vector) by increasing the promoter strength that governs the expression level of the system (for example, changing the high constitutive GI1.6 promoter of the current system to the stronger constitutive PL.6 promoter) or by moving the current *E. coli* IspG system to a higher-copy vector (pBBR1MCS-5 vector, gentamicin resistance encoded, compatible with other vectors required for a comparable high DXP flux strain).

The relevant increased promoter strength test strain has the genotype: BL21 pgl+PL.2-lower MVA pathway GI1.6-yidi PL.6-dxs GI1.6-dxr+PL.6-fldA-ispG/pCL (Spec 50)+PTac Anabaena ispH/pK184 (Kan 50)+PTrc-truncated alba IspS/pTrc H is (Carb 50). The relevant increased vector copy-number test strain proposed has the genotype: BL21 pgl+ PL.2-lower MVA pathway GI1.6-yidi PL.6-dxs GI1.6-dxr+ GI.6-fldA-ispG/pBBR1MCS-5 (Gent 10)+PTac Anabaena ispH/pK184 (Kan 50)+PTrc-truncated alba IspS/pTrc His (Carb 50). An additional increased vector copy-number test strain proposed has the genotype: BL21 pgl+PL.2-lower MVA pathway GI1.6-yidi PL.6-dxs GI1.6-dxr+GI.6-fldA-ispG/pCL (Spec 50)+GI.6-fldA-ispG/pBBR1MCS-5 (Gent 10)+PTac Anabaena ispH/pK184 (Kan 50)+PTrc-truncated alba IspS/pTrc His (Carb 50). The control strain is BL21 pgl+PL.2-lower MVA pathway GI1.6-yidi PL.6-dxs GI1.6-dxr+GI1.6-fldA-ispG/pCL (Spec 50)+PTac Anabaena ispH/pK184 (Kan 50)+PTrc-truncated alba IspS/pTrc His (Carb 50).

Without being bound by theory, with respect to IspH activity not being limiting, as described above, IspH activity in existing *E. coli* IspG system and *T. elongatus* IspG system isoprene producing strains does not appear limiting. To determine insufficient an IspH activity level that would hamper isoprene output and confound the interpretation of any effects on IpsG activity, one of skill in the art looks for the phenotypes described above and use biochemical assays. In the absence of any indication that IpsH activity is limiting, isoprene production is used as a means to reflect improved IspG activity. IspG levels can be determined by immunoblot to confirm expression levels associated with the measured activities.

What is claimed is:

1. A recombinant cell capable of producing isoprene, the cell comprising: (a) a nucleic acid encoding a first 1-hydroxy-2-methyl-2-(E)-butenyl 4-diphosphate synthase (IspG) polypeptide of a first species and a nucleic acid encoding a second IspG polypeptide of a second species, wherein the second species differs from the first species; (b) a nucleic acid encoding at least one 1-deoxyxylulose-5-phosphate (DXP) pathway enzyme, and (c) a nucleic acid encoding an isoprene synthase polypeptide, wherein the cell produces isoprene at a greater titer as compared to a cell comprising a nucleic acid encoding an IspG polypeptide of a single species.

2. The recombinant cell of claim 1, wherein the first IspG polypeptide is a *T. elongatus* IspG polypeptide.

3. The recombinant cell of claim 1, wherein the second IspG polypeptide is an *E. coli* IspG polypeptide.

4. The recombinant cell of claim 1, further comprising a nucleic acid encoding an iron-sulfur cluster-interacting redox polypeptide.

5. The recombinant cell of claim 4, wherein the iron-sulfur cluster-interacting redox polypeptide is selected from ferredoxin and flavodoxin.

6. The recombinant cell of claim 1, further comprising a nucleic acid encoding a 1-deoxyxylulose-5-phosphate (DXP) pathway associated polypeptide.

7. The recombinant cell of claim 6, wherein the 1-deoxyxylulose-5-phosphate (DXP) pathway associated polypeptide is a chaperone protein.

8. The recombinant cell of claim 1, wherein the cell further comprises at least one heterologous nucleic acid encoding an isopentenyl-diphosphate delta-isomerase (IDI) polypeptide or at least one copy of an endogenous nucleic acid encoding an IDI polypeptide.

9. The recombinant cell of claim 1, wherein the cell further comprises at least one heterologous nucleic acid encoding a mevalonate (MVA) pathway polypeptide or at least one copy of an endogenous nucleic acid encoding a MVA pathway polypeptide.

10. The recombinant cell of claim 8, wherein the cell further comprises at least one heterologous nucleic acid encoding a mevalonate (MVA) pathway polypeptide or at least one copy of an endogenous nucleic acid encoding a MVA pathway polypeptide.

11. The recombinant cell of claim 1, wherein the isoprene synthase polypeptide is a plant isoprene synthase polypeptide.

12. The recombinant cell of claim 11, wherein the isoprene synthase polypeptide is a polypeptide from *Pueraria* or *Populus* or a hybrid, *Populus alba* × *Populus tremula*.

13. The recombinant cell of claim 11, wherein the isoprene synthase polypeptide is selected from the group consisting of *Pueraria montana* or *Pueraria lobata*, *Populus tremuloides*, *Populus alba*, *Populus nigra*, and *Populus trichocarpa*.

14. The recombinant cell of claim 11, wherein the plant isoprene synthase polypeptide is a kudzu isoprene synthase polypeptide.

15. The recombinant cell of claim 1, wherein the cell is a bacterial, algal, fungal or yeast cell.

16. The recombinant cell of claim 15, wherein the cell is a bacterial cell.

17. The bacterial cell of claim 16, wherein the bacterial cell is a gram-positive bacterial cell or gram-negative bacterial cell.

18. The bacterial cell of claim 17, wherein the bacterial cell is selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells.

19. The recombinant cell of claim 1, wherein the additional 1-deoxyxylulose-5-phosphate (DXP) pathway enzyme is selected from the group of: 1-deoxyxylulose-5-phosphate synthase (DXS), 1-deoxy-D-xylulose-5-phosphate reductoisomerase (DXR), 4-diphosphocytidyl-2C-methyl-D-erythritol synthase (MCT), 4-diphosphocytidyl-2-C-methyl-D-erythritol kinase, (CMK), 2C-methyl-D-erythritol 2,4-cyclodiphosphate synthase (MCS), 1-hydroxy-2-methyl-2-(E)-butenyl 4-diphosphate reductase (HDR/IspH), and isopentenyl-diphosphate delta isomerase (IDI).

20. The recombinant cell of claim 19, wherein the additional 1-deoxyxylulose-5-phosphate (DXP) pathway enzyme is selected from the group of: 1-deoxyxylulose-5-phosphate synthase (DXS), 1-deoxy-D-xylulose-5-phosphate reductoisomerase (DXR), 1-hydroxy-2-methyl-2-(E)-butenyl 4-diphosphate reductase (HDR/IspH), and isopentenyl-diphosphate delta isomerase (IDI).

* * * * *

SEQUENCE LISTING

<160> NUMBER OF SEQ ID NOS: 8

<210> SEQ ID NO 1
<211> LENGTH: 125
<212> TYPE: DNA
<213> ORGANISM: Artificial Sequence
<220> FEATURE:
<223> OTHER INFORMATION: Synthetic Construct

<400> SEQUENCE: 1
aattcatata aaaacatac agataaccat ctgcggtgat aaattatctc tggcggtgtt        60
gacataaata ccactggcgg tgatactgag cacatcagca ggacgcactg accaccatga      120
aggtg                                                                  125

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
cacttgagtt tatacgcatc                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
gatgcgtata aactcaagtg                                                   20

<210> SEQ ID NO 4
<211> LENGTH: 32
<212> TYPE: DNA
<213> ORGANISM: Artificial Sequence
<220> FEATURE:
<223> OTHER INFORMATION: Synthetic Construct

<400> SEQUENCE: 4
gcggcagcca tatgcaaacg ttgccaagcc ca                                     32

<210> SEQ ID NO 5
<211> LENGTH: 35
<212> TYPE: DNA
<213> ORGANISM: Artificial Sequence
<220> FEATURE:
<223> OTHER INFORMATION: Synthetic Construct

<400> SEQUENCE: 5
tagcagccgg atccttatgg atctacccat ctacc                                  35

<210> SEQ ID NO 6
<211> LENGTH: 18
<212> TYPE: DNA
<213> ORGANISM: Artificial Sequence
<220> FEATURE:
<223> OTHER INFORMATION: Synthetic Construct

<400> SEQUENCE: 6
aggcgattaa gttgggta                                                     18

<210> SEQ ID NO 7
<211> LENGTH: 18
<212> TYPE: DNA
<213> ORGANISM: Artificial Sequence
<220> FEATURE:
<223> OTHER INFORMATION: Synthetic Construct

<400> SEQUENCE: 7
ggctcgtata atgtgtgg                                                     18

<210> SEQ ID NO 8
<211> LENGTH: 6351
<212> TYPE: DNA
<213> ORGANISM: Artificial Sequence
<220> FEATURE:
<223> OTHER INFORMATION: Synthetic Construct

<400> SEQUENCE: 8

```
cgataagcta gcttcacgct gccgcaagca ctcagggcgc aagggctgct aaaggaagcg      60
gaacacgtag aaagccagtc cgcagaaacg gtgctgaccc cggatgaatg tcagctactg     120
ggctatctgg acaagggaaa acgcaagcgc aaagagaaag caggtagctt gcagtgggct     180
tacatggcga tagctagact gggcggtttt atggacagca agcgaaccgg aattgccagc     240
tggggcgccc tctggtaagg ttgggaagcc ctgcaaagta aactggatgg ctttcttgcc     300
gccaaggatc tgatggcgca ggggatcaag atctgatcaa gagacaggat gaggatcgtt     360
tcgcatgatt gaacaagatg gattgcacgc aggttctccg gccgcttggg tggagaggct     420
attcggctat gactgggcac aacagacaat cggctgctct gatgccgccg tgttccggct     480
gtcagcgcag gggcgcccgg ttcttttttgt caagaccgac ctgtccggtg ccctgaatga     540
actccaagac gaggcagcgc ggctatcgtg gctggccacg acgggcgttc cttgcgcagc     600
tgtgctcgac gttgtcactg aagcgggaag ggactggctg ctattgggcg aagtgccggg     660
gcaggatctc ctgtcatctc accttgctcc tgccgagaaa gtatccatca tggctgatgc     720
aatgcggcgg ctgcatacgc ttgatccggc tacctgccca ttcgaccacc aagcgaaaca     780
tcgcatcgag cgagcacgta ctcggatgga agccggtctt gtcgatcagg atgatctgga     840
cgaagagcat caggggctcg cgccagccga actgttcgcc aggctcaagg cgcggatgcc     900
cgacggcgag gatctcgtcg tgacccatgg cgatgcctgc ttgccgaata tcatggtgga     960
aaatggccgc ttttctggat tcatcgactg tggccggctg ggtgtggcgg accgctatca    1020
ggacatagcg ttggctaccc gtgatattgc tgaagagctt ggcggcgaat gggctgaccg    1080
cttcctcgtg ctttacggta tcgccgctcc cgattcgcag cgcatcgcct tctatcgcct    1140
tcttgacgag ttcttctgag cgggactctg gggttcggat gataagctgt caaacatgag    1200
aattacaact tatatcgtat ggggctgact tcaggtgcta catttgaaga gataaattgc    1260
actgaaatct agaaatattt tatctgatta ataagatgat cttcttgaga tcgttttggt    1320
ctgcgcgtaa tctcttgctc tgaaaacgaa aaaaccgcct tgcagggcgg ttttttcgaag    1380 gttctctgag ctaccaactc tttgaaccga ggtaactggc ttggaggagc gcagtcacca    1440
aaacttgtcc tttcagttta gccttaaccg gcgcatgact tcaagactaa ctcctctaaa    1500
tcaattacca gtggctgctg ccagtggtgc ttttgcatgt ctttccgggt tggactcaag    1560
acgatagtta ccggataagg cgcagcggtc ggactgaacg gggggttcgt gcatacagtc    1620
cagcttggag cgaactgcct acccggaact gagtgtcagg cgtggaatga acaaacgcg     1680 gccataacag cggaatgaca ccggtaaacc gaaaggcagg aacaggagag cgcacgaggg    1740
agccgccagg gggaaacgcc tggtatcttt atagtcctgt cgggtttcgc caccactgat    1800
ttgagcgtca gatttcgtga tgcttgtcag ggggcggag cctatggaaa aacggctttg     1860 cctcctcgcgt tatcccctga ttctgtggat aaccgtatta ccgcctttga gtgagctgat    1920
accgctcgcc gcagccgaac gaccgagcgc agcgagtcag tgagcgagga agcggaagag    1980
cgcccaatac gcaaaccgcc tctccccgcg cgttggccga ttcattaatg cagctggcac    2040
gacaggtttc ccgactggaa aggaattctg ttgacaatta atcatcggct cgtataatgt    2100
```

```
gtggaattgt gagcggataa caatttcaca caggaaacag attacggatc cctggagttt    2160
aaacatatgg atactaaaac ctttaaacgt acgttgcaac actccgaaaa ctacaatcgg    2220
aaagggttcg gtcatcaggc ggaggttgca actcaactgc aatcagaata tcagagttct    2280
ttgattcagg aaatccgcga tcgcaactac actcttcaac gtggggatgt cacgataaga    2340
cttgctcagg catttggctt ctgctggggt gttgaacgtg cggtcgcgat ggcttatgag    2400
acccggaagc attttccaac tgaacgcatc tggattacca acgaaatcat tcacaatccg    2460
agcgtcaacc agcggatgca ggaaatgcaa gtgggcttta taccagtaga ggcgggcaac    2520
aaggatttta gcgtagtcgg caataatgac gtcgttatcc tgccagcctt tggcgcttct    2580
gtgcaagaga tgcagctttt atctgaaaaa ggatgtaaaa tagttgatac cacatgtccg    2640
tgggtatcaa aagtctggaa taccgtggaa aagcataaaa agggggatca tacctctata    2700
atacatggca aatataaaca cgaagaaacg attgccacaa gttccttcgc gggtaaatat    2760
ctcatcgtcc ttaaccttaa ggaagcacaa tacgttgctg actacattct gcatgggggt    2820
aatcgtgagg agttcttaca gaaatttgca aaagcatgct cggcgggctt tgaccccgat    2880
agagatcttg aaagagttgg cattgccaat cagacaacaa tgttgaaagg agagaccgaa    2940
cagatcggta aacttttttga acataccatg ctgcaaaaat acggacccgt ggagttaaat    3000
caacattttc agtccttcaa tacaatttgc gacgctaccc aggaacggca ggacgccatg    3060
ctggagctgg tacaagaaaa tttggacctc atgatcgtga tcggaggttt taattcttcc    3120
aacacaacac agctccaaca gattagccag gaacggggtc tgccgtccta tcatattgat    3180
gtagttgagc gtattaaaag cataaactcg atagagcacc ggcagttaaa cggagagttg    3240
gtcactacgg aaaattggct gcctgcgggc aaaattgtcg taggtgtaac aagtggcgcg    3300
agtacaccag ataaggtggt tgaagacgtg atcgaaaaga tctttgcgct taaagcaaca    3360
gcggccgtct tttaacccga tccatttgag gagtaagcca tgcaaacgtt gccaagccca    3420
gttcaagcta caccaacgga aacagctatt gttagacgca aaacccgccc ggttccgata    3480
ggctccgttg ttattggtgg cggccatccc gtggctgttc agtcaatgat taacgaagac    3540
actctggata tcgaaggttc tgttgctgca attcggcgct tacacgagat cggttgcgag    3600
atcgtacgtg tgactgtacc ttcattagca cacgcgaaag caatggaaga gattcgggat    3660
cggctttata aaacgtacaa accggtcccc ttagttgccg acgtgcatca taacggaatg    3720
aaaatcgcgt tagaggttgc caagtacgtg gacaatgtgc gcattaatcc tggattatac    3780
gtgtttgaga agccaaaacc aaatcgcacg gagtacactc aagctgaatt tgacgagatt    3840
ggcgcgaaaa tccgtgaaac gttggaacca ctggtaattt cactgcggga tcagggaaag    3900
tcgatgcgca ttggcgttaa tcatggcagt ctggcggaac ggatgctgtt tacctatggc    3960 gatacccccag agggtatggt agagagtgca cttgagttta tacgcatctg tgaaagtctc    4020
aacttctata acttagaaat ttcccttaaa gctagccgcg tcccggttat gatagccgcc    4080
aatcggctta tggttaagcg catggacgag ctgggtatgg attatccgtt gcatctcgga    4140
gtgactgagg caggtgatgg tgaatatggc cgtattaaaa gcacagcagg cattgcaaca    4200
ctgctggcgg aaggaattgg agacacaatc cgtgtttcat tgactgaagc tccggaaaag    4260
gaaatccccg tgtgctatgg catccttcaa gccctcggtc tccgccgcac catggtagaa    4320
tatgtagctt gcccgtcgtg tggtcggaca ttgtttaacc tggaagaggt tctgcacaag    4380
gtgagagaag cgactaaaca cctgacggga ctgaatattg cggttatggg atgtattgta    4440
aatggacctg gcgaaatggc cgatgcagac tacggctatg taggtaaaca gccgggatat    4500
```

-continued

```
ataagtctttt accgcggccg ggaagaagtc aagaaagtgc ccgaggccga gggcgttgca    4560
gctctggtcg aactgataaa agcggatggt agatgggtag atccataagt ggagctcccc    4620
ggtaccgtgg acgaggttta atatggcgac gtataaagtc acactggtcc gtccggatgg    4680
cagcgaaacg accatcgatg ttccggagga cgaatacata ctggatgtcg ccgaagaaca    4740
aggtctggat ctcccgtttt cttgtcgcgc cggtgcctgc tctacctgtg ctggcaaatt    4800
gttggaggga gaagtcgatc aaagcgacca gagcttcttg gatgacgatc agatcgaaaa    4860
aggattcgtg cttacttgtg tggcctaccc ccgttcggac tgcaagatct tgacgaacca    4920
agaggaggag ctgtactaag aggtcgacga cgcatgcatt aacagaggtt agtatgtata    4980
atgccactaa ctctcgctca cgtatgttcc ggtacgaagt tgtggggctg cgccaaacgg    5040
cggagacgga gaaacaaat tacgcgatca gaaactctgg ctcgcagttc tttaatgtgc     5100
cttatgaccg catgaaccag tttatgcagc agatcactcg gtgggcggt aaaattgtca    5160 gtattcagcc ccttaacgga accgtggccc cacttgctgc aaccacggag ccagctgcca    5220
ataacggagc tgcacctgtg aaagaaaaga aagtcgatat accggtcaac atctaccgtc    5280
ccaataatcc ctgcataggt aaggttatta gcaacgagga actggtccgg gaaggcggtg    5340
agggtacggt gaaacatatt atctttgata tatcggggac cgaattacgt tacttggaag    5400
ggcagtcaat cggtatcatt cccgcgggca cggacgcgaa cggtaaacca cataagctgc    5460
gtctgtattc cattgcttcc acaagacatg gtgactttca ggatgacaag acggtgtcct    5520
tatgcgtacg gagattagaa tacaaagata aagagaccgg ggagaccatt tatggcgtgt    5580
gcagttcgta tcttaatcag ttacagcctg gagatgaagt caaaatcaca ggtcctgttg    5640
ggaaagaaat gcttctctct gacgacccag aagcgactat tattatgctg ctaccggca    5700 ctggaatagc gccatttcgg gcatttttat ggcggatgtt caaagagaac aacccggatt    5760
accagttcaa aggccttgcg tggctgttct ttggcgtcgc ttatactgcc aatatcctgt    5820
ataaggacga gcttgaagct atccaagccc agtatcccga tcattttcgg ttaacctacg    5880
cgatttcccg tgaacaaaaa accccggacg gagggaaaat gtacatccag ggtcggatcg    5940
cagagcacgc tgatgaaatc tggcaactgc tgcaaaagaa aaacacccac gtgtacatgt    6000
gtggcctgcg tgggatggaa cctggaatag acgaggccat gaccgcagcg gccgcgaaaa    6060
acggagctga ctggcaggag tttctgaaag gtacgctgaa aaaggaaggc agatggcatg    6120
tcgaaactta ttaactgcag tacaaataaa aaaggcacgt cagatgacgt gcctttttc     6180 ttgaagcttg gcactggccg tcgttttaca acgtcgtgac tgggaaaacc ctggcgttac    6240
ccaacttaat cgccttgcag cacatccccc tttcgccagc tggcgtaata gcgaagaggc    6300
ccgcaccgat cgcccttccc aacagttgcg cagcctgaat ggcgaatggc g             6351
```